(12) United States Patent
Chappell et al.

(10) Patent No.: US 7,442,785 B2
(45) Date of Patent: Oct. 28, 2008

(54) SESQUITERPENE SYNTHASE GENE AND PROTEIN

(75) Inventors: Joe Chappell, Lexington, KY (US); Brian Greenhagen, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 10/899,356

(22) Filed: Jul. 26, 2004

(65) Prior Publication Data

US 2006/0218661 A1 Sep. 28, 2006

Related U.S. Application Data

(60) Provisional application No. 60/489,514, filed on Jul. 24, 2003.

(51) Int. Cl.
*C12N 15/09* (2006.01)
*C12N 15/29* (2006.01)

(52) U.S. Cl. .................................... 536/23.6; 536/23.1

(58) Field of Classification Search .............. 536/23.1, 536/23.2, 23.6; 435/183, 320.1, 419, 468; 800/298, 316
See application file for complete search history.

(56) References Cited

U.S. PATENT DOCUMENTS

| 4,693,905 | A | 9/1987 | Japikse et al. |
|---|---|---|---|
| 4,973,485 | A | 11/1990 | Rich et al. |
| 5,260,086 | A | 11/1993 | Downton et al. |
| 6,495,193 | B2 | 12/2002 | Hiramoto et al. |
| 2003/0185956 | A1 | 10/2003 | Gradley |
| 2003/0203090 | A1 | 10/2003 | Kotachi et al. |
| 2005/0210549 | A1* | 9/2005 | Schalk et al. ............... 800/287 |

FOREIGN PATENT DOCUMENTS

WO WO 2004/031376 A2 4/2004

OTHER PUBLICATIONS

Marutama T. et al. Biol. Pharm Bull. 2001; vol. 24 pp. 1171-1175.*
Tholl D. Current Opinion in Plant Biology; 2006, vol. 9, pp. 297-304.*
Louzada et al., "Identification of a gene highly expressed in juice vesicles of mature Rio Red grapefruit using deferential display" Citrus Center , Texas A & M (Aug. 16, 2001).
Accession No. AF411120, Citrus x paradisi, www.ncbi.nlm.nih.gov (2002).

* cited by examiner

*Primary Examiner*—Russell Kallis
(74) *Attorney, Agent, or Firm*—David Kohn; Catalyst Law Group

(57) ABSTRACT

The invention relates to sesquiterpene synthases and methods for their production and use. Particularly, the invention provides nucleic acids comprising the nucleotide sequence of citrus valencene synthase (CVS) which codes for at least one CVS. The invention further provides nucleic acids comprising the nucleotide sequence coding for amino acid residues forming the tier 1 and tier 2 domains of CVS. The invention also provides for methods of making and using the nucleic acids and amino acids of the current invention.

4 Claims, 17 Drawing Sheets

| Synthase Product | FIRST TIER | | | | | | J/K Loop | | | | SECOND TIER | | | | | | | | | | | | | | | | | |
|---|---|---|---|---|---|---|---|---|---|---|---|---|---|---|---|---|---|---|---|---|---|---|---|---|---|---|---|---|
| | 264 | 273 | 403 | 404 | 440 | 441 | 520 | 525 | 527 | 528 | 20 | 256 | 270 | 298 | 302 | 372 | 376 | 401 | 402 | 407 | 436 | 441 | 445 | 448 | 512 | 515 | 516 | 519 | 529 |
| 5-epi-aristolochene | R | W | T | Y | C | D | Y | D | Y | T | F | R | C | S | D | V | Y | T | T | L | S | R | D | T | L | I | V | T | H |
| premnaspirodiene | R | W | T | Y | C | D | Y | D | Y | T | F | R | C | S | D |  | Y | T | S | L | N | R | D | T | L | I |  | T | H |
| valencene | R | W |  | Y | C | D | Y | D | Y | T | F | R |  | S | D | V | Y |  | C |  | N | R | D |  | L |  |  | I | H |

FIG. 4

Nucleotide (DNA) sequence for Citrus Valencene Synthase gene (CVS)

SEQ ID NO.: 1

Length: 1710 nt

```
  64 atgtcgtctggagaaacatttcgtcctactgcagatttccatcct
 109 agtttatggagaaaccatttcctcaaggtgcttctgatttcaag
 154 acagttgatcatactgcaactcaagaacgacacgaggcactgaaa
 199 gaagaggtaaggagaatgataacagatgctgaagataagcctgtt
 244 cagaagttacgcttgattgatgaagtacaacgcctgggggtggct
 289 tatcactttgagaagaaatagaagatgcaatactaaaattatgt
 334 ccaatctatattgacagtaatagagctgatctccacaccgtttcc
 379 cttcattttcgattgcttaggcagcaaggaatcaagatttcatgt
 424 gatgtgtttgagaagttcaaagatgatgagggtagattcaagtca
 469 tcgttgataaacgatgttcaaggatgttaagtttgtacgaggca
 514 gcatacatggcagttcgcggagaacatatattagatgaagccatt
 559 gctttcactaccactcacctgaagtcattggtagctcaggatcat
 604 gtaaccctaagcttgcggaacagataaatcatgctttataccgt
 649 cctcttcgtaaaaccctaccaagattagaggcgaggtattttatg
 694 tccatgatcaattcaacaagtgatcatttatacaataaaactctg
 739 ctgaattttgcaaagttagattttaacatattgctagagccgcac
 784 aaggaggaactcaatgaattaacaaagtggtggaaagatttagac
 829 ttcactacaaaactaccttatgcaagagacagattagtggagtta
 874 tattttgggatttagggacatacttcgagcctcaatatgcattt
 919 gggagaaagataatgacccaattaaattacatattccatcata
 964 gatgatacttatgatgcgtatggtacacttgaagaactcagcctc
1009 tttactgaagcagttcaaagatggaatattgaggccgtagatatg
1054 cttccagaatacatgaaattgatttacaggacactcttagatgct
1099 tttaatgaaattgaggaagatatggccaagcaaggaagatcacac
1144 tgcgtacgttatgcaaaagaggagaatcaaaaagtaattggagca
1189 tactctgttcaagccaaatggttcagtgaaggttacgttccaaca
1234 attgaggagtatatgccattgcactaacaagttgtgcttacaca
1279 ttcgtcataacaaattccttccttggcatgggtgattttgcaact
1324 aaagaggttttgaatggatctccaataaccctaaggttgtaaaa
1369 gcagcatcagttatctgcagactcatggatgacatgcaaggtcat
1414 gagtttgagcagaagagaggacatgttgcgtcagctattgaatgt
1459 tacacgaagcagcatggtgtctctaaggaagaggcaattaaaatg
1504 tttgaagaagaagttgcaaatgcatggaaagatattaacgaggag
1549 ttgatgatgaagccaaccgtcgttgcccgaccactgctcgggacg
1594 attcttaatcttgctcgtgcaattgatttatttacaaagaggac
1639 gacggctatacgcattcttacctaattaaagatcaaattgcttct
1684 gtgctaggagaccacgttccattttga 1710
```

FIG. 5

Amino acid sequence of Citrus Valencene Synthase (CVS)

SEQ ID NO.: 4

Length: 548 aa

| Synthase Product | FIRST TIER | | | | | | J/K Loop | | | |
|---|---|---|---|---|---|---|---|---|---|---|
| | 264 | 273 | 403 | 404 | 440 | 444 | 520 | 525 | 527 | 528 |
| 5-epi-aristolochene | R | W | T | Y | C | D | Y | D | Y | T |
| premnaspirodiene | R | W | T | Y | C | D | Y | D | Y | T |
| valencene | R | W | A | Y | C | D | Y | D | Y | T |

FIG. 11

| Absolute SEQ ID NO 4 | Comparative SEQ ID NO 7 | Nucleotide SEQ ID NO.: 5 |
|---|---|---|
| R264 | R264 | 853aga |
| W273 | W273 | 880ttg |
| A403 | A403 | 1270gct |
| Y404 | Y404 | 1273tac |
| C441 | C440 | 1384tcg |
| D445 | D444 | 1396gat |
| Y522 | Y520 | 1627tac |
| D526 | D525 | 1639gac |
| Y528 | Y527 | 1645tat |
| T529 | T528 | 1648acg |

FIG. 12

| Absolute SEQ ID NO 4 | Comparative SEQ ID NO 8 | SEQ ID NO.: 6 |
|---|---|---|
| F13 | F20 | 100ttc |
| R266 | R266 | 859aga |
| L270 | L270 | 871tta |
| S298 | S298 | 955tcc |
| D302 | D302 | 967gat |
| V372 | V372 | 1177gta |
| Y376 | Y376 | 1189tac |
| S401 | S401 | 1264agt |
| C402 | C402 | 1267tgt |
| V407 | V407 | 1282gtc |
| A437 | A436 | 1372gca |
| R442 | R441 | 1387aga |
| D446 | D445 | 1399gac |
| G449 | G448 | 1408ggt |
| L514 | L512 | 1603ctt |
| A517 | A515 | 1612gca |
| I518 | I516 | 1615att |
| I521 | I519 | 1624att |
| H530 | H529 | 1651cat |

FIG. 13

| R264 |
|---|
| W273 |
| A403 |
| Y404 |
| C441 |
| D445 |
| Y522 |
| D526 |
| Y528 |
| T529 |

FIG. 14a

| R264 |
|---|
| W273 |
| A403 |
| Y404 |
| C440 |
| D444 |
| Y520 |
| D525 |
| Y527 |
| T528 |

FIG. 14b

| F13 | F20 |
|---|---|
| R266 | R266 |
| L270 | L270 |
| S298 | S298 |
| D302 | D302 |
| V372 | V372 |
| Y376 | Y376 |
| S401 | S401 |
| C402 | C402 |
| V407 | V407 |
| A437 | A436 |
| R442 | R441 |
| D446 | D445 |
| G449 | G448 |
| L514 | L512 |
| A517 | A515 |
| I518 | I516 |
| I521 | I519 |
| H530 | H529 |

FIG. 15a        FIG. 15b

| | | |
|---|---|---|
| TEAS protein | 1 | MASAAVANYEEEIVRPVADFSPSLWGDQFLS--FSIKNQVAEKYAQEIEA 48 |
| CVS-chappell | 1 | MSSG------ETFRPTADFHPSLWRNHFLKGASDFKTVDHTATQERHEA 43 |
| TEAS protein | 49 | LKEQTRNMLLATGMKLADTLNLIDTIERLGISYHFEKEIDDILDQIYNQ- 97 |
| CVS-chappell | 44 | LKEEVRRMITDAEDKPVQKLRLIDEVQRLGVAYHFEKEIEDAILKLCPIY 93 |
| TEAS protein | 98 | -NSNCNDLCTSALQFRLLRQHGFNISPEIFSKFQDENGKFKESLASDVLG 146 |
| CVS-chappell | 94 | IDSNRADLHTVSLHFRLLRQQGIKISCDVFEKFKDDEGRFKSSLINDVQG 143 |
| TEAS protein | 147 | LLNLYEASHVRTHADDILEDALAFSTIHLES--AAPHLKSPLREQVTHAL 194 |
| CVS-chappell | 144 | MLSLYEAAYMAVRGEHILDEAIAFTTTHLKSLVAQDHVTPKLAEQINHAL 193 |
| TEAS protein | 195 | EQCLHKGVPRVETRFFISSIYDKE-QSKNNVLLRFAKLDFNLLQMLHKQE 243 |
| CVS-chappell | 194 | YRPLRKTLPRLEARYFMSMINSTSDHLYNKTLLNFAKLDFNILLEPHKEE 243 |
| TEAS protein | 244 | LAQVSRWWKDLDFVTTLPYARDRVVECYFWALGVYFEPQYSQARVMLVKT 293 |
| CVS-chappell | 244 | LNELTKWWKDLDFTTKLPYARDRLVELYFWILGTYFEPQYAFGRKIMTQL 293 |
| TEAS protein | 294 | ISMISIVDDTFDAYGTVKELEAYTDAIQRWDINEIDRLPDYMKISYKAIL 343 |
| CVS-chappell | 294 | NYILSIIDDTYDAYGTLEELSLFTEAVQRWNIEAVDMLPEYMKLIYRTLL 343 |
| TEAS protein | 344 | DLYKDYEKELSSAGRSHIVCHAIERMKEVVRNYNVESTWFIEGYTPPVSE 393 |
| CVS-chappell | 344 | DAFNEIEEDMAKQGRSHCVRYAKEENQKVIGAYSVQAKWFSEGYVPTIEE 393 |
| TEAS protein | 394 | YLSNALATTTYYYLATTSYLGMKS-ATEQDFEWLSKNPKILEASVICRV 442 |
| CVS-chappell | 394 | YMPIALTSQAYTFVITNSFLGMGDFATKEVFEWISNNPKVVKAASVICRL 443 |
| TEAS protein | 443 | IDDTATYEVEKSRGQIATGIECCMRDYGISTKEAMAKFQNMAETAWKDIN 492 |
| CVS-chappell | 444 | MDDMQGHEFEQKRGHVASAIECYTKQHGVSKEEAIKMFEEEVANAWKDIN 493 |
| TEAS protein | 493 | EGLLR-PTPVSTEFLTPILNLARIVEVTYIHNLDGYTHPEKVLKPHIINL 541 |
| CVS-chappell | 494 | EERLMMKPTVVARPLLGTILNLARAIDFLYKE-DDGYTH-SYLIKDQIASV 541 |
| TEAS protein | 542 | LVDSIKIN 549 |
| CVS-chappell | 542 | LGDHVPF- 548 |

FIG. 16

| TEAS Amino Acid Number | CVS Absolute SEQ ID NO.: 4 | Comparative SEQ ID NOS 7 and 8 |
|---|---|---|
| TIER 1 | | |
| R264 | R264 | R264 |
| W273 | W273 | W273 |
| T403 | A403 | A403 |
| Y404 | Y404 | Y404 |
| C440 | C441 | C440 |
| D444 | D445 | D444 |
| Y520 | Y522 | Y520 |
| D525 | D526 | D525 |
| Y527 | Y528 | Y527 |
| T528 | T529 | T528 |
| TIER 2 | | |
| F20 | F13 | F20 |
| R266 | R266 | R266 |
| C270 | L270 | L270 |
| S298 | S298 | S298 |
| D302 | D302 | D302 |
| V372 | V372 | V372 |
| Y376 | Y376 | Y376 |
| T401 | S401 | S401 |
| T402 | C402 | C402 |
| L407 | V407 | V407 |
| S436 | A437 | A436 |
| R441 | R442 | R441 |
| D445 | D446 | D445 |
| T448 | G449 | G448 |
| L512 | L514 | L512 |
| I515 | A517 | A515 |
| V516 | I518 | I516 |
| T519 | I521 | I519 |
| H529 | H530 | H529 |

FIG. 17

SESQUITERPENE SYNTHASE GENE AND PROTEIN

RELATED APPLICATION

Benefit of priority under 35 U.S.C. 119(e) is claimed herein to U.S. Provisional Application No. 60/489,514, filed Jul. 24, 2003. The disclosure of the above referenced application is incorporated by reference in its entirety herein.

FIELD OF THE INVENTION

This invention relates generally to the field of production of valencene and nootkatone, and more particularly relates to the discovery of a valencene synthase gene and related protein, which provides a pathway for generating highly pure valencene which can be converted into the flavorant, nootkatone.

BACKGROUND

Terpenes are a diverse family of compounds with carbon skeletons composed of five-carbon isoprene units. Approximately 20,000 different terpenes and terpenoids (compounds of terpene origin whose carbon skeleton has been altered or rearranged) have been identified to date, representing only a small fraction of the estimated natural variation. Terpenes are commonly isolated from the essential oils of plants. Essential oils often have pleasant tastes or aromas, and they are widely used as flavorings, deodorants, and medicines.

Sesquiterpenes are terpenes with 15 carbon atoms (three isoprene units). The plant kingdom contains the highest diversity of sesquiterpenes. Often they play a role in defense of the plants against pathogens, insects and herbivores and for attraction of pollinating insects.

Valencene (1,2,3,5,6,7,8,8a-octahydro-7-isopropenyl-1, 8a-dimethyl-naphthalene) and nootkatone (4,4a,5,6,7,8-hexahydro-6-isopropenyl-4,4a-dimethyl-2(3H)-naphtalenone) are just two examples of sesquiterpenes that are derived from cyclization of the ubiquitous pyrophosphate intermediate farnesyl diphosphate. Nootkatone is formed by the oxidation of valencene.

Valencene and nootkatone are compounds of natural origin, and are natural constituents of citrus oils, such as orange and grapefruit. Because of its excellent organoleptic qualities and in particular its typical grapefruit taste, nootkatone is a widely used ingredient in perfumery and the flavor industry. Alternatively, nootkatone may be used as an insecticide. Valencene, the starting material for the generation of nootkatone (either biologically or chemically), is also used as a flavorant and fragrance.

Several methods to purify sesquiterpenes, such as valencene and nootkatone, from citrus fruits or to maintain high levels of these sesquiterpenes in citrus fruit extracts have been described in the prior art. These methods are described below.

Japikse et al., in U.S. Pat. No. 4,693,905, claimed a method of extracting concentrated orange flavor and aroma compositions from natural orange essence oil by using a dense solvent gas. Their procedure entailed (a) contacting natural orange essence oil with a solvent gas having a temperature between its critical temperature and 100° C., and having a reduced pressure between about 0.56 and about 1.31 (where reduced pressure is defined as the extraction pressure of the solvent gas divided by its critical pressure), to extract flavor and aroma compounds; (b) separating the solvent gas and dissolved compounds from the remaining undissolved compounds; and (c) separating the dissolved compounds from the solvent gas.

Rich, in U.S. Pat. No. 4,973,485, discloses a method of producing aqueous orange stripper essences and orange stripper oils with high ratios of valencene to the less desirable orange flavor compounds. This procedure involves the following steps: (a) heating an orange fed juice stream to a temperature of 37.7° C. to 71° C.; (b) stripping the heated feed juice with steam at a steam: soluble solids ratio of 0.3 to 1.5, at a temperature of 37.7° C. to 71° C. and at a stripping column pressure of less than 9 inches of Hg, absolute; (c) condensing the stripped volatiles at a temperature of 40.6° C. to −196° C.; (d) centrifuging the condensate in a continuous stacked disk hermetic centrifuge to produce two clear phases; and (e) removing the aqueous orange stripper essence phase.

In U.S. Pat. No. 5,260,086 Downton et al. describe a process for making an aseptic citrus sensible pulp/juice slurry by extracting and removing juice from citrus juice containing sensible pulp. After this process is complete, flavorants, such as valencene are added to make up for those that are lost during this extraction process.

Hiramoto et al., in U.S. Pat. No. 6,495,193 prepares a citrus flavor from a low-boiling part of a cold pressed oil by a hydrate alcohol solvent extraction. To maintain the stability of the flavor, a stabilizing coumarin analogue component is added.

In a US Patent Application, publication number US 20030185956, Gradley claims a separation method for extracting desired sesquiterpene aroma compounds, such as valencene and nootkatone, from an aqueous phase by separating the aqueous mixture from a water-immiscible hydrophobic phase by means of a hydrophilic membrane and allowing the desired components to move out off the aqueous phase through the membrane and into the hydrophobic phase.

Kotachi et al., in US Patent Application, publication number 20030203090, teaches of a process for preparing orange oil useful as fragrance or flavor material, by mixing raw material oil containing valencene with a high-boiling solvent having a boiling point exceeding 240° C. under normal pressure, to give a mixture, and fractionally distilling the mixture obtained.

Nootkatone is a high demand, high value flavorant added to many of the commercial soft drinks sold worldwide. Currently, the practice of extracting nootkatone from citrus pulp and rind is considered an expensive and somewhat unreliable process. Nootkatone can be synthesized by the oxidation of valencene. The valencene starting material is expensive and is easily degraded during evaporative heat concentration processes typically used to remove the bulk of water from the feed juice. Thus, current methods to purify valencene from citrus fruits are costly, difficult, and are limited by what the fruit can deliver. Moreover, such methods are vulnerable to interruptions in the supply of citrus fruits, which is dependent on the weather. A frost or hailstorm in a major citrus fruit growing region such as Florida can interrupt the supply. Furthermore, methods to produce nootkatone that consume valencene are quite costly, and thus not commercially desirable. Therefore, there is a need for an alternative means for preparing valencene and nootkatone.

SUMMARY OF THE INVENTION

In one embodiment, the invention relates to isolated nucleic acids that encode a sesquiterpene synthase. The invention provides an isolated nucleic acid selected from: (a) a nucleic acid comprising the nucleotide sequence substantially as set out in SEQ ID NO: 1; (b) a nucleic acid encoding the polypeptide substantially set out in SEQ ID NO: 4; and (c) a nucleic acid that hybridizes to the nucleic acid of (a) or (b)

under low stringency conditions, wherein the polypetide encoded by said nucleic acid is a sesquiterpene synthase. Other embodiments include: a polypeptide encoded by a nucleic acid of the invention; a host cell comprising a nucleic acid of the invention; a non-human organism modified to harbor a nucleic acid of the invention; and methods of producing a polypeptide comprising culturing host cells of the invention.

In another embodiment, the invention provides an isolated polypeptide comprising an amino acid sequence substantially as set out in SEQ ID NO: 4.

In a further embodiment, the invention provides a vector comprising at least one nucleic acid chosen from (a) a nucleic acid comprising the nucleotide sequence substantially as set out in SEQ ID NO: 1; (b) a nucleic acid encoding the polypeptide substantially set out in SEQ ID NO: 4; and (c) a nucleic acid that hybridizes to the nucleic acid of (a) or (b) under low stringency conditions, wherein the polypeptide encoded by said nucleic acid is a sesquiterpene synthase. Other embodiments include, methods of making a recombinant host cell comprising introducing a vector of the invention into a host cell.

In a further embodiment, the invention relates to isolated nucleic acids that encode a sesquiterpene synthase. The invention provides an isolated nucleic acid selected from: (a) a nucleic acid comprising the nucleotide sequence substantially as set out in SEQ ID NO: 5 or SEQ ID NO.: 6; (b) a nucleic acid encoding the polypeptide substantially set out in SEQ ID NO: 7 or SEQ ID NO.: 8; and (c) a nucleic acid that hybridizes to the nucleic acid of (a) or (b) under low stringency conditions, wherein the polypeptide encoded by said nucleic acid is a sesquiterpene synthase. Other embodiments include: a polypeptide encoded by a nucleic acid of the invention; a host cell comprising a nucleic acid of the invention; a non-human organism modified to harbor a nucleic acid of the invention; and methods of producing a polypeptide comprising culturing host cells of the invention.

In another embodiment, the invention provides an isolated polypeptide comprising an amino acid sequence substantially as set out in SEQ ID NO: 7 or SEQ ID NO.: 8.

In a further embodiment, the invention provides a vector comprising nucleic acid chosen from (a) a nucleic acid comprising the nucleotide sequence substantially as set out in SEQ ID NO: 5 or SEQ ID NO.: 6; (b) a nucleic acid encoding the polypeptide substantially set out in SEQ ID NO: 7 or SEQ ID NO.: 8; and (c) a nucleic acid that hybridizes to the nucleic acid of (a) or (b) under low stringency conditions, wherein the polypeptide encoded by said nucleic acid is a sesquiterpene synthase. Other embodiments include, methods of making a recombinant host cell comprising introducing a vector of the invention into a host cell.

In one embodiment, the invention provides a method of making at least one sesquiterpene synthase comprising culturing a host cell modified to contain at least one nucleic acid sequence under conditions conducive to the production of said at least one sesquiterpene synthase. In one embodiment, the at least one nucleic acid is chosen from (a) a nucleic acid comprising the nucleotide sequence substantially as set out in SEQ ID NO: 1, SEQ ID NO.: 5 or SEQ ID NO.: 6; (b) a nucleic acid encoding the polypeptide substantially set out in SEQ ID NO: 4, SEQ ID NO.: 7 or SEQ ID NO.: 8; and (c) a nucleic acid that hybridizes to the nucleic acid of (a) or (b) under low stringency conditions, wherein the polypeptide encoded by said nucleic acid is a sesquiterpene synthase. The host may be chosen from, for example, plants, microorganisms, bacterial cells, yeast cells, plant cells, and animal cells.

In another embodiment the invention provides a method of making at least one terpenoid comprising:

1) contacting at least one acyclic pyrophosphate terpene precursor with at least one polypeptide encoded by a nucleic acid of the current invention. In one embodiment, the nucleic acid is chosen from (a) a nucleic acid comprising the nucleotide sequence substantially as set out in SEQ ID NO.: 1, SEQ ID NO.: 5 or SEQ ID NO.: 6; (b) a nucleic acid encoding the polypeptide substantially set out in SEQ ID NO: 4, SEQ ID NO.: 7 or SEQ ID NO.: 8; and (c) a nucleic acid that hybridizes to the nucleic acid of (a) or (b) under low stringency conditions, wherein the polypetide encoded by said nucleic acid is a sesquiterpene synthase, 2) isolating at least one terpenoid produced in 1).

In one embodiment, the at least one terpenoid is chosen from the group consisting of sesquiterpene.

In a further embodiment, the at least one acyclic pyrophosphate terpene precursor is farnesyl-diphosphate (FPP). The sesquiterpene produced by the methods of the invention include, but are not limited to, valencene, valencene derivatives, valencene fragments, and compounds having the citrus valencene carbon skeleton.

BRIEF DESCRIPTION OF THE DRAWINGS

FIG. 4 illustrates a sequence alignment of amino acids lining the active site (1st tier) and those within 3 Å of the active site residues (2nd tier) of TEAS with the corresponding positions of CVS. For uniformity, the TEAS amino acids numbering was used, and thus the corresponding CVS amino acids renumbered—termed comparative numbering. The 1st tier residues lie within 3 Å of a substrate analog co-crystallized within the TEAS enzyme and includes residues making up the J/K loop which clamps down over the active site upon substrate binding. The corresponding residues within CVS (valencene synthase) were initially identified by primary sequence alignment, then visual inspection of the relevant CVS sequences overlaid on the TEAS 3-dimensional structure. Residues different from TEAS are highlighted.

FIG. 5 shows SEQ ID NO.: 1, which is the DNA sequence for the citrus valencene synthase gene from *Citrus paradis* isolated in the current invention.

FIG. 6 shows SEQ ID NO.: 4, which is the protein sequence for the citrus valencene synthase from *Citrus paradisi*.

FIG. 11 is a sequence alignment of amino acids lining the active site (1st tier) of TEAS with the corresponding positions of HPS and CVS. The 1 st tier residues lie within 3 Å of a substrate analog co-crystallized within the TEAS enzyme and includes residues making up the J/K loop which clamps down over the active site upon substrate binding. The corresponding residues within the other terpene synthases were initially identified by primary sequence alignment, then visual inspection of the relevant sequences overlaid on the TEAS 3-dimensional structure. Residues in CVS differing from TEAS are highlighted.

FIG. 12 shows SEQ ID NO.: 5, which is the DNA sequence from SEQ ID NO.: 1 corresponding to the amino acids forming Tier 1. Comparative numbering from Tier 1 amino acid residues is also shown (SEQ ID NO.: 7).

FIG. 13 shows SEQ ID NO.: 6, which is the DNA sequence from SEQ ID NO.: 1 corresponding to the amino acids forming Tier 2. Comparative numbering from Tier 2 amino acid residues is also shown (SEQ ID NO.: 8).

FIG. 14a shows the absolute amino acid sequence from SEQ ID NO.: 4 corresponding to the Tier 1 amino acid residues. FIG. 14b shows the comparative amino acid sequence of the Tier 1 amino acid residues (SEQ ID NO.: 7)

FIG. 15a shows the absolute amino acid sequence from SEQ ID NO.: 4 corresponding to Tier 2 amino acid residues. FIG. 15b shows the comparative amino acid sequence of the Tier 2 amino acid residues (SEQ ID NO.: 8).

FIG. 16 is a sequence alignment of the amino acid sequence of TEAS active site compared to the amino acid sequence of the CVS active site. The alignment maximizes residue similarities and introduce gaps where necessary. Absolute amino acid numbering is shown for CVS, thus amino acid numbering from SEQ ID NO.: 4 is shown for CVS.

FIG. 17 is a chart showing the TEAS Tier 1 and Tier 2 amino acid residues in column 1; the CVS Tier 1 and Tier 2 amino acid residues with absolute numbering in column 2; and the CVS Tier 1 and Tier 2 amino acid residues with comparative numbering in column 3.

DETAILED DESCRIPTION OF THE INVENTION

Abbreviations and Terms

Figure 1:
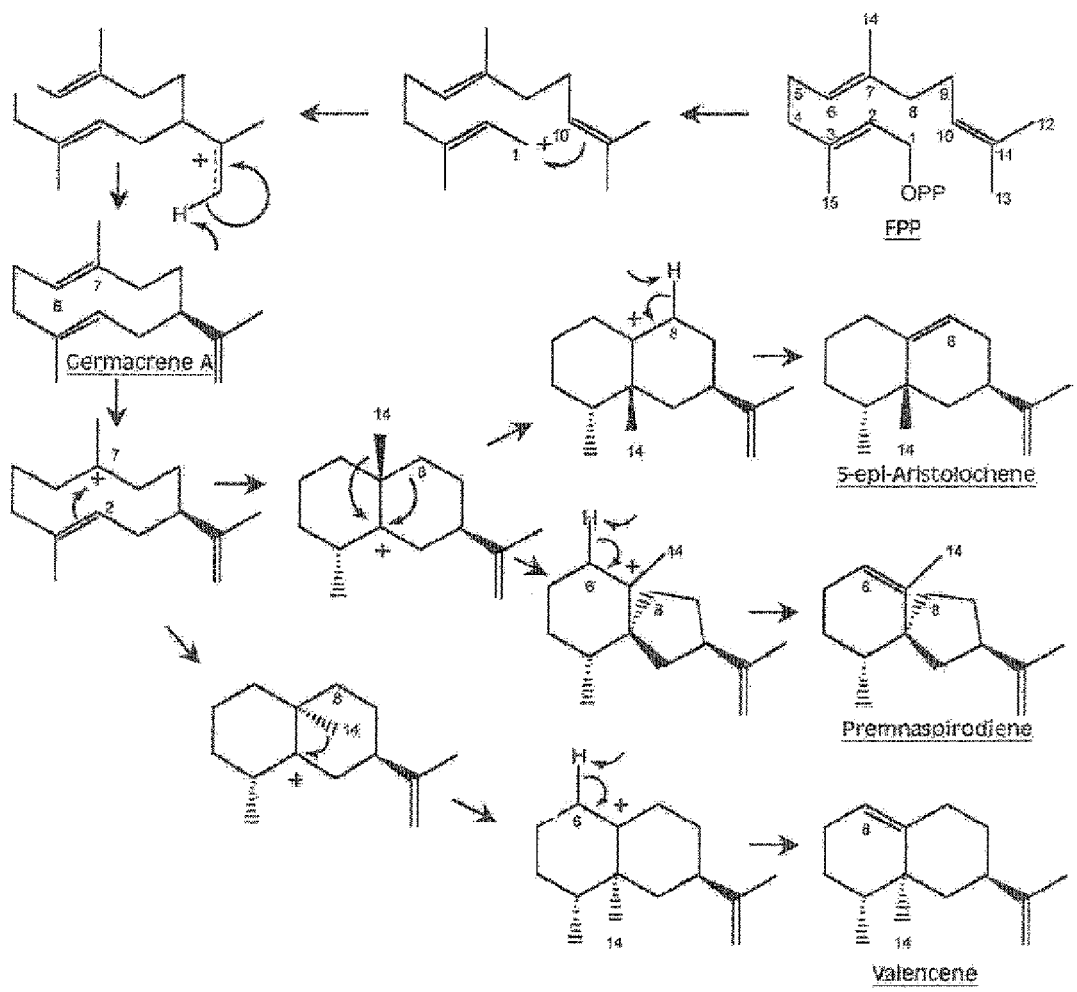
FIG. 1 shows the conversion of FPP to the sesquiterpene reaction products 5-epi-aristolochene, premnaspirodiene and valencene catalyzed by *Nicotiana tabacum* epi-aristolochene synthase (TEAS), *Hyoscyamus muticus* premnaspirodiene synthase (HPS), and *Citrus paradisi* valencene synthase (CVS), respectively.

In accordance with the present invention and as used herein, the following terms and abbreviations are defined with the following meanings, unless explicitly stated otherwise. These explanations are intended to be exemplary only. They are not intended to limit the terms as they are described or referred to throughout the specification. Rather, these explanations are meant to include any additional aspects and/or examples of the terms as described and claimed herein.

The following abbreviations are used herein:

As used herein, a "derivative" is any compound obtained from a known or hypothetical compound and containing essential elements of the parent substance.

The phrase "substantially identical" means that a relevant sequence is at least 70%, 75%, 80%, 85%, 90%, 92%, 95% 96%, 97%, 98%, or 99% identical to a given sequence. By way of example, such sequences may be allelic variants, sequences derived from various species, or they may be derived from the given sequence by truncation, deletion, amino acid substitution or addition. Percent identity between two sequences is determined by standard alignment algorithms such as ClustalX when the two sequences are in best alignment according to the alignment algorithm.

As used herein, the term "hybridization" or "hybridizes" under certain conditions is intended to describe conditions for hybridization and washes under which nucleotide sequences that are significantly identical or homologous to each other remain bound to each other. Appropriate hybridization conditions can be selected by those skilled in the art with minimal experimentation as exemplified in Ausubel, F. A., et al., eds., Current Protocols in Molecular Biology Vol. 2, John Wiley and Sons, Inc., New York (1995). Additionally, stringency conditions are described in Sambrook et al. Molecular Cloning: A Laboratory Manual, 2nd ed., Cold Spring Harbor Laboratory Press, New York (1989). Variations on the conditions for low, moderate, and high stringency are well known in the art and may be used with the current invention.

The terms "nucleic acid" or "nucleic acid molecule" refer to a deoxyribonucleotide or ribonucleotide polymer in either single-or double-stranded form, and unless otherwise limited, would encompass known analogs of natural nucleotides that can function in a similar manner as naturally occurring nucleotides. A "nucleotide sequence" also refers to a polynucleotide molecule or oligonucleotide molecule in the form of a separate fragment or as a component of a larger nucleic acid. The nucleotide sequence or molecule may also be referred to as a "nucleotide probe." Some of the nucleic acid molecules of the invention are derived from DNA or RNA isolated at least once in substantially pure form and in a quantity or concentration enabling identification, manipulation, and recovery of its component nucleotide sequence by standard biochemical methods. Examples of such methods, including methods for PCR protocols that may be used herein, are disclosed in Sambrook et al. Molecular Cloning: A Laboratory Manual, 2nd ed., Cold Spring Harbor Laboratory Press, New York (1989), Ausubel, F. A., et al., eds., Current Protocols in Molecular Biology, John Wiley and Sons, Inc., New York (1987), and Innis, M., et al. (Eds.) PCR Protocols: A Guide to Methods and Applications, Academic Press, San Diego, Calif. (1990). Reference to a nucleic acid molecule also includes its complement as determined by the standard Watson-Crick base-pairing rules, with uracil (U) in RNA replacing thymine (T) in DNA, unless the complement is specifically excluded.

As described herein, the nucleic acid molecules of the invention include DNA in both single-stranded and double-stranded form, as well as the DNA or RNA complement thereof. DNA includes, for example, DNA, genomic DNA, chemically synthesized DNA, DNA amplified by PCR, and combinations thereof. Genomic DNA, including translated, non-translated and control regions, may be isolated by conventional techniques, e.g., using any one of the cDNAs of the invention, or suitable fragments thereof, as a probe, to identify a piece of genomic DNA which can then be cloned using methods commonly known in the art.

Polypeptides encoded by the nucleic acids of the invention are encompassed by the invention. As used herein, reference to a nucleic acid "encoding" a protein or polypeptide encompasses not only cDNAs and other intronless nucleic acids, but also DNAs, such as genomic DNA, with introns, on the assumption that the introns included have appropriate splice donor and acceptor sites that will ensure that the introns are spliced out of the corresponding transcript when the transcript is processed in a eukaryotic cell. Due to the degeneracy of the genetic code wherein more than one codon can encode the same amino acid, multiple DNA sequences can code for the same polypeptide. Such variant DNA sequences can result from genetic drift or artificial manipulation (e.g., occurring during PCR amplification or as the product of deliberate mutagenesis of a native sequence). Deliberate mutagenesis of a native sequence can be carried out using numerous techniques well known in the art. For example, oligonucleotide-directed site-specific mutagenesis procedures can be employed, particularly where it is desired to mutate a gene such that predetermined restriction nucleotides or codons are altered by substitution, deletion or insertion. Exemplary methods of making such alterations are disclosed by Walder et al. (Gene 42:133,1986); Bauer et al. (Gene 37:73, 1985); Craik (BioTechniques, Jan. 12-19, 1985); Smith et al. (Genetic Engineering: Principles and Methods, Plenum Press, 1981); Kunkel (Proc. Natl. Acad. Sci. USA 82:488,1985); Kunkel et al. (Methods in Enzymol. 154.367, 1987). The present invention thus encompasses any nucleic acid capable of encoding a protein of the current invention.

The current invention provides for isolated polypeptides. As used herein, the term "polypeptides" refers to a genus of polypeptide or peptide fragments that encompass the amino acid sequences identified herein, as well as smaller fragments. Alternatively, a polypeptide may be defined in terms of its antigenic relatedness to any peptide encoded by the nucleic acid sequences of the invention. Thus, in one embodiment, a polypeptide within the scope of the invention is defined as an amino acid sequence comprising a linear or 3-dimensional epitope shared with any peptide encoded by the nucleic acid sequences of the invention. Alternatively, a polypeptide within the scope of the invention is recognized by an antibody that specifically recognizes any peptide encoded by the nucleic acid sequences of the invention. Antibodies are defined to be specifically binding if they bind polypeptides of the invention with a $K_a$ of greater than or equal to about $10^7$ $M^{-1}$, such as greater than or equal to $10^8$ $M^{-1}$. As used herein, the term "isolated," in reference to polypeptides or proteins, means that the polypeptide or protein is substantially removed from polypeptides, proteins, nucleic acids, or other macromolecules with which it, or its analogues, occurs in nature. Although the term "isolated" is not intended to require a specific degree of purity, typically, the protein will be at least about 75% pure, more typically at least about 90% pure, preferably at least about 95% pure, and more preferably at least about 99% pure.

A polypeptide "variant" as referred to herein means a polypeptide substantially homologous to a native polypeptide, but which has an amino acid sequence different from that encoded by any of the nucleic acid sequences of the invention because of one or more deletions, insertions or substitutions. Variants can comprise conservatively substituted sequences, meaning that a given amino acid residue is replaced by a residue having similar physiochemical characteristics. See Zubay, Biochemistry, Addison-Wesley Pub. Co., (1983). It is a well-established principle of protein and peptide chemistry that certain amino acids substitutions, entitled "conservative" amino acid substitutions, can frequently be made in a protein or a peptide without altering either the confirmation or the function of the protein or peptide. Such changes include substituting any of isoleucine (I), valine (V), and leucine (L) for any other of these amino acids; aspartic acid (D) for glutamic acid (E) and vice versa; glutamine (Q) for asparagine (N) and vice versa; and serine (S) for threonine (T) and vice versa.

The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

The effects of such substitutions can be calculated using substitution score matrices such PAM120, PAM-200, and PAM-250 as discussed in Altschul, (J. Mol. Biol. 219:55565 (1991)). Other such conservative substitutions, for example, substitutions of entire regions having similar hydrophobicity characteristics, are well known.

Naturally-occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the valencene synthase of the invention may be used to attain desired enhanced or reduced enzymatic activity, modified regiochemistry or stereochemistry, or altered substrate utilization or product distribution. A variant or site direct mutant may be made by any methods known in the art. Variants and derivatives of native polypeptides can be obtained by isolating naturally-occurring variants, or the nucleotide sequence of variants, of other or same plant lines or species, or by artificially programming mutations of nucleotide sequences coding for native citrus polypeptides.

In one embodiment, the invention contemplates: vectors comprising the nucleic acids of the invention. A vector as used herein includes any recombinant vector including but not limited to viral vectors, bacteriophages and plasmids.

Expression vectors containing a nucleic acid sequence of the invention can be prepared using well known methods and include a cDNA sequence encoding the polypeptide operably linked to suitable transcriptional or translational regulatory nucleotide sequences. Examples of regulatory sequences include transcriptional promoters, operators, or enhancers, mRNA ribosomal binding sites, and appropriate sequences which control transcription and translation initiation and termination. Nucleotide sequences are "operably linked" when the regulatory sequence functionally relates to the cDNA sequence of the invention. Expression vectors, regulatory elements and the construction thereof are well known in the art, and therefore are not limited to those recited above.

In addition, sequences encoding appropriate signal peptides that are not naturally associated with the polypeptides of the invention can be incorporated into expression vectors. For example, a DNA sequence for a signal peptide (secretory) leader can be fused in-frame to a nucleotide sequence of the invention so that the polypeptide of the invention is initially translated as a fusion protein comprising the signal peptide. A signal peptide that is functional in the intended host cells enhances extracellular secretion of the expressed polypeptide. The signal peptide can be cleaved from the polypeptide upon secretion from the cell. In some cases, signal peptides are cleaved in two or more stages; this is also within the scope of the invention where appropriate.

Fusions of additional peptide sequences at the amino and carboxyl terminal ends of the polypeptides of the invention can be used with the current invention.

In one embodiment, the invention includes a host cell comprising a nucleic acid of the invention. Another embodiment of the invention is a method of making a recombinant host cell comprising introducing the vectors of the invention, into a host cell. In a further embodiment, a method of producing a polypeptide comprising culturing the host cells of the invention under conditions to produce the polypeptide is contemplated. In one embodiment the polypeptide is recovered. The methods of the invention include methods of making at least one valencene synthase of the invention comprising culturing a host cell comprising a nucleic acid of the invention, and recovering the sesquiterpene synthase accumulated.

Suitable host cells for expression of polypeptides of the invention are well known in the art, and include, but are not limited to, prokaryotes, yeast, higher eukaryotic cells, or combinations thereof. (See for example, Pouwels et al. Cloning Vectors: A Laboratory Manual, Elsevier, New York (1985)). Cell-free translation systems, also well known in the art, could also be employed to produce the disclosed polypeptides using RNAs derived from DNA constructs disclosed herein.

Host cells may be modified by any methods known in the art for gene transfer including, for example, the use of delivery devices such as lipids and viral vectors, naked DNA, electroporation and particle-mediated gene transfer.

In one embodiment, the cDNAs of the invention may be expressed in such a way as to produce either sense or antisense RNA. The expression of antisense RNA can be used to down-modulate the expression of the protein encoded by the mRNA to which the antisense RNA is complementary.

A further embodiment of the invention is methods of making terpenoids and sesquiterpene compounds, for example, using the nucleotides and polypeptides of the invention.

As used herein an acyclic pyrophosphate terpene precursor is any acyclic pryrophosphate compound that is a precursor to the production of at least one terpene including but not limited to geranyl-pyrophosphate (GPP), farnesyl-diphosphate (FPP) and geranylgeranyl-pyrophosphate (GGPP).

In one embodiment, the distribution of products or the actual products formed may be altered by varying the pH at which the synthase contacts the acyclic pyrophosphate terpene precursor.

Also within the practice of the invention is an organism (e.g., microorganism or plant) that is used to construct a platform for high level production of a substrate of sesquiterpene synthases (e.g., FPP) and the introduction of a nucleic acid of the invention into the organism.

Unless otherwise indicated, nucleic acids of the invention that are DNA encompass both cDNA (DNA reverse transcribed from mRNA and lacking introns) and isolated genomic DNA (DNA that can contain introns.)

In one embodiment, the nucleic acids of the invention are used to create other nucleic acids coding for sesquiterpene synthases. For example, the invention provides for a method of identifying a sesquiterpene synthases comprising constructing a DNA library using the nucleic acids of the invention, screening the library for nucleic acids which encode for at least one sesquiterpene synthase. The DNA library using the nucleic acids of the invention may be constructed by any process known in the art where DNA sequences are created using the nucleic acids of the invention as a starting point, including but not limited to DNA suffling. In such a method, the library may be screened for sesquiterpene synthases using a functional assay to find a target nucleic acid that encodes a sesquiterpene synthase. The activity of a sesquiterpene synthase may be analyzed using, for example, the methods described herein. In one embodiment, high through put screening is utilized to analyze the activity of the encoded polypeptides.

As used herein a "nucleotide probe" is defined as an oligonucleotide or polynucleotide capable of binding to a target nucleic acid of complementary sequence through one or more types of chemical bonds, through complementary base pairing, or through hydrogen bond formation.

A "target nucleic acid" herein refers to a nucleic acid to which the nucleotide probe or molecule can specifically hybridize. The probe is designed to determine the presence or absence of the target nucleic acid, and the amount of target nucleic acid. The target nucleic acid has a sequence that is significantly complementary to the nucleic acid sequence of the corresponding probe directed to the target so that the probe and the target nucleic acid can hybridize. Preferably, the hybridization conditions are such that hybridization of the probe is specific for the target nucleic acid. As recognized by one of skill in the art, the probe may also contain additional nucleic acids or other moieties, such as labels, which may not specifically hybridize to the target. The term target nucleic acid may refer to the specific nucleotide sequence of a larger nucleic acid to which the probe is directed or to the overall sequence (e.g., gene or mRNA). One skilled in the art will recognize the full utility under various conditions.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements.

Figure 2:
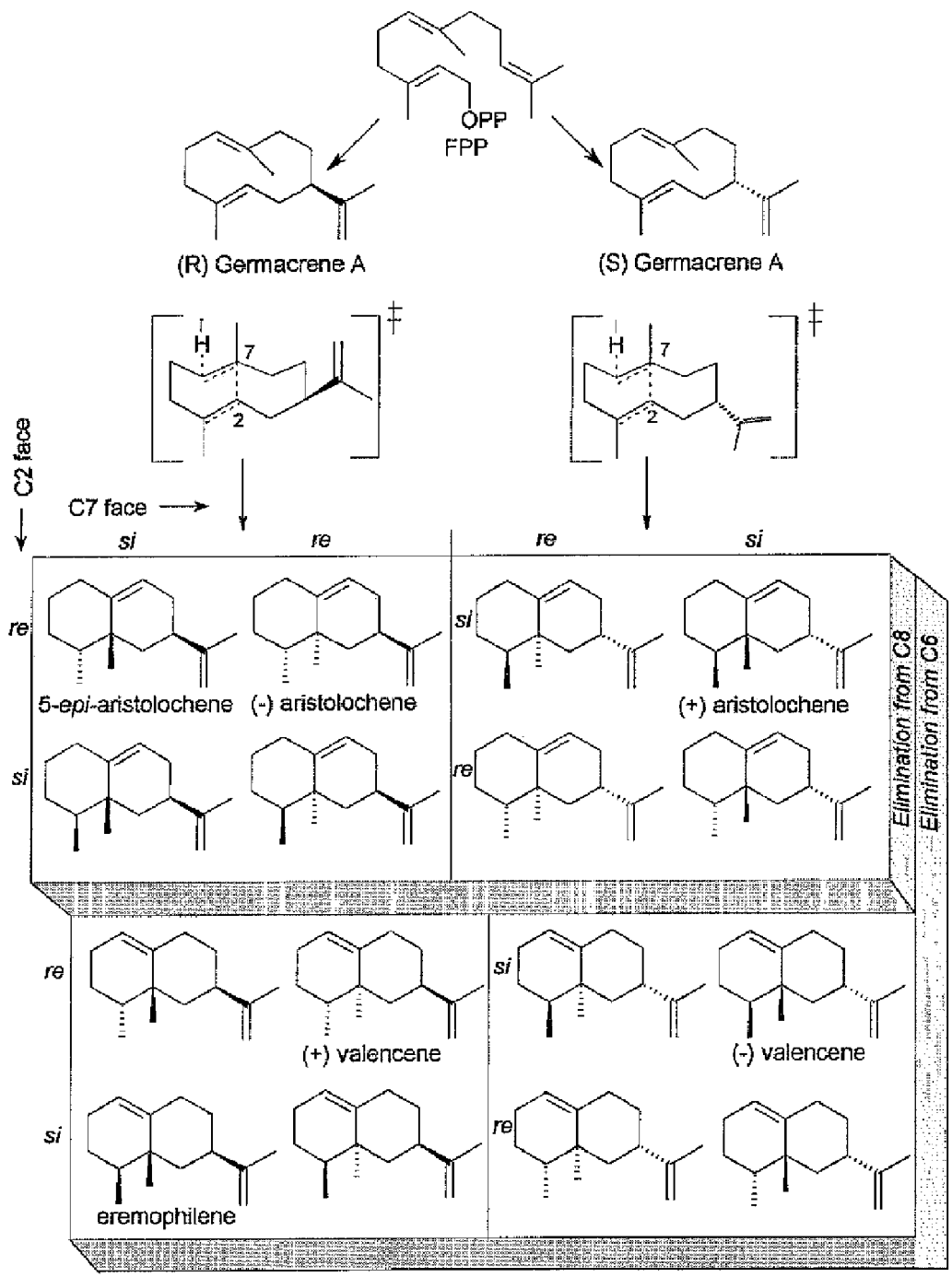
FIG. 2 illustrates a mechanism for the enzyme catalyzed development of regio- and enantio-specificity in eremophilanes. Upon loss of the diphosphate from C1 and generation of the initial carbocation, a chiral center arises from the first attack on either the si or re face of sp2 hybridized C10 yielding either (10R)-germacrene A or (10S)-germacrene A. Two additional chiral centers develop upon formation of an internal bond between C2 and C7. This process of proton-initiated, internal cyclization (illustrated as transition states) requires that the p-orbitals of sp2 hybridized C2 and C7 face and align with each other. The 4 possible combinations of overlapping orbitals are dependent on the orientation of the respective p orbitals either above or below the plane of the eudesmalyl carbocation intermediate. The possible re and si orientations of the C2 p-orbitals are given on the vertical axis of the diagram and those for C7 depicted on the horizontal axis. These orientations direct the stereochemistry of the ensuing methyl migrations and hydride shifts (not illustrated) and define, as a consequence, the final chirality of the methyl substitutions at C2 and C3. Subsequent to these rearrangements, a tertiary carbocation centered at C7 is formed (an eremophilyl cation, not shown) and alternate elimination of a proton from C6 or C8 give two subclasses of double bond regioisomers, illustrated as layers. Known eremophilanes are noted by their common name.
Figure 3:
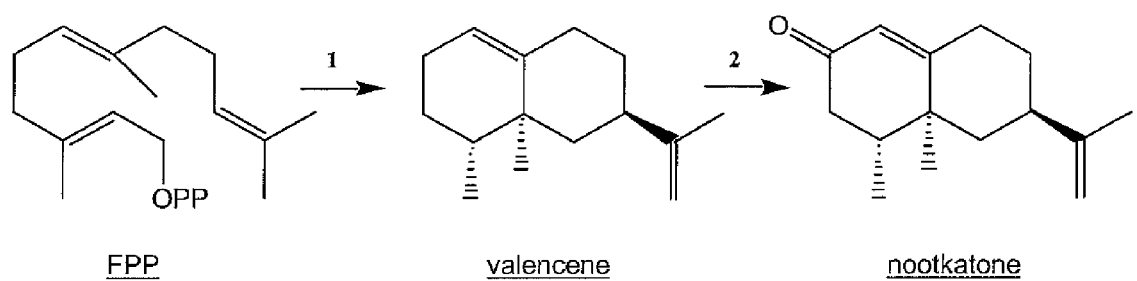
FIG. 3 illustrates a proposed pathway for the biosynthesis of nootkatone in citrus. The scheme suggests at least two steps, the first step is catalyzed by the sesquiterpene synthase of the current invention, denoted as "1" in the figure, which leads to the production of valencene and the second step consisting of a regio-specific hydroxylation, followed by oxidation. The second step could be catalyzed by a single multifunctional hydroxylase or could involve sequential enzyme mediated reactions, and which are denoted as "2" in the figure.

Hundreds of genes with similarity to terpene synthases are readily observed in protein sequence or keyword searches of GenBank with a significant percentage of these currently annotated as terpene synthase-like. In order to isolate synthase genes coding for enzymes that share catalytic features in common with tobacco 5-epi-aristolochene synthase (TEAS) or *Hyoscyamus muticus* premnaspirodiene synthase (HPS) (FIG. 1), Inventors considered possible biosynthetic routes for all isomeric forms of the eremophilane-type sesquiterpenes (FIG. 2). (+)Valencene and its oxygenated derivative nootkatone (FIG. 3) were readily recognized as high value natural products isolated from citrus used as flavor enhancers. To identify the terpene synthase responsible for the biosynthesis of valencene, Inventors screened sequences from several citrus (*Citrus* x *paradisi* and *Citrus junos*) EST sequencing projects deposited in GenBank (www.ncbi.nlm.nih.gov/Genbank/index.html) for sequences similar to TEAS and HPS. Two sequences were observed, one from *Citrus junos* (accession AF288465) and the other from *Citrus paradisi* (accession AF411120). The predicted proteins from both of these cDNAs were between about 40% identical and about 60% similar to TEAS, but the *C. junos* cDNA predicted a protein that was missing segments of 10 and 12 amino acids relative to TEAS. The isolated protein from *Citrus paradisi* was 45% homologous with TEAS (see below). Inventors, therefore, focused on the isolation and characterization of a full-length cDNA corresponding to AF411120 from grapefruit (*C. paradisi*).

The cDNA isolated by Inventors is a terpene synthase gene, the protein product of which is citrus valencene synthase (CVS). The following non-limiting examples describe Inventors isolation, and expression of the CVS gene, and also further characterize the CVS protein via enzyme activity assays and pH assays. Applicants have further characterized the key amino acid residues comprising the active domain of the CVS protein via these enzyme activity assays and via a comparison to other eremophilane-type sesquiterpenes, in particular TEAS, HPS and delta-cadinene synthase from cotton.

Sequence comparisons between terpene synthases have suggested that simple sequence alignments are not sufficient to identify amino acids or protein regions contributing to catalytic specificity. Inventors aligned the residues forming the active region of the isolated CVS with the residues forming active region of TEAS. In order to perform a comparative analysis of the two active regions (CVS and TEAS), the absolute amino acid number for CVS was shifted to correspond with the TEAS amino acid numbers. FIG. 16 illustrates the alignment of CVS amino acid residues with those of TEAS and maintains the numbering of TEAS and the numbering for CVS. Inventors then adjusted the amino acid numbering of CVS to match that of TEAS (comparative numbering). Tier 1 and Tier 2 amino acid numbering follows this comparative numbering, thus, Tier 1 and Tier 2 amino acids would also have the comparative numbering shift (SEQ ID NOS.: 7 and 8, respectively). FIG. 17. Thus, as is used herein the term "absolute numbering" refers to the sequence number of the CVS amino acid residues in SEQ ID NO.: 1 and the nucleotide numbering in SEQ ID NO.: 4. As used herein, the term "comparative numbering" refers to the sequence numbering of the amino acid residues based on the TEAS numbering, which were designated as a means to compare TEAS and CVS active site amino acid residues, and neighboring residues (Tiers 1 and 2). Nucleic acid residues coding for the amino acids comprising Tier 1 (SEQ ID NO.: 5) and Tier 2 (SEQ ID NO.: 6) are based on the nucleotide sequence of SEQ ID NO.: 1, and are absolute numbers.

As is seen in FIG. 4 and FIG. 11 wherein Inventors compared the amino acids of TEAS, HPS and CVS, only a single amino acid difference was observed within the 1st tier residues of TEAS and CVS; however 8 amino acid differences were observed within the second tier residues of TEAS and CVS. CVS exhibits an alanine at position 403 rather than a threonine as is found in TEAS. Using this discovery, Inventors have further compared amino acid residues surrounding the active site and discovered that these amino acids, termed Tier 2 amino acids and discussed below, influence the catalytic outcome of these enzymes.

For clarity in this disclosure, Tier 1 amino acids are the amino acid residues that form the catalytic pocket in a sesquiterpene synthase, and Tier 2 amino acids are those amino acids that are within a few angstroms of the Tier 1 residues, preferably between the range of about 1 angstrom and about 5 angstroms, more preferably between the range of about 2 angstrom and about 4 angstrom and most preferably 3 angstrom. In this disclosure, the amino acid residue sequence for Tier 1 and Tier 2, based on the amino acid residue sequence of SEQ ID NO.: 4, but adjusted for a comparative analysis with TEAS, are SEQ ID NO.: 7, shown in FIG. 14b, and SEQ ID NO.: 8, shown in FIG. 15b. The corresponding nucleotide sequence for the Tier 1 and Tier 2 amino acid residues, therefore, are based on the nucleotide sequence of SEQ ID NO.: 1, and are SEQ ID NO.: 5, shown in FIG. 12, and SEQ ID NO.: 6, shown in FIG. 13. The recited amino acid residue sequences, recited position number, corresponding nucleotide and nucleotide position number are based on the full protein and nucleotide sequences recited in SEQ ID NO.1 and SEQ ID NO.: 4, respectively. Because the current invention accounts for frame shift mutations, fusion proteins, fragments, degeneracy of the genetic code and other events that can change these recited sequences and positions without loosing the spirit of the current invention, the sequences and positions of these events are included in the current invention.

Inventors then analyzed the second tier amino acid residues for the TEAS and CVS protein sequences. Second tier residues, those amino acid R groups within a few Å of the 1st tier amino acids, were examined for differences between TEAS and CVS (FIG. 4). Three positions within the 2nd tier exhibited common differences between TEAS and CVS (positions 402, 436 and 516), as well as substitutions unique to CVS (270, 401, 407, 448, 515) relative to TEAS. A role for 2nd tier residues in catalysis, then, includes determining whether a synthase produces a C7-C8 double bond or a C6-C7 double bond. This arises because the final proton abstraction occurred at C6 rather than C8, a spatial distance of 3-4 Å or approximately the diameter of a methyl group. Equally important, regio-specific abstraction necessarily arises from proper geometric positioning of C8 or C6 of the eremophylyl cation in proximity to an active site residue or activated water molecule capable of the final abstraction. Positioning of the final reaction intermediate therefore comes about by simple spatial allowances created by the presence or absence of slightly bulkier R-groups on one side of the active site pocket balanced by the converse on the opposite site of the pocket. For instance, the poly-threonine sequence at positions 401-403 of TEAS is replaced by the small amino acids serine, cysteine and alanine in CVS, which appear balanced by a smaller amino acid (valine 516) on the opposite side of the active site pocket in TEAS and the larger amino acid isoleucine in CVS. Without being bound by any theory, differences between sesquiterpene synthases, particularly TEAS and CVS may be due to alterations of the active site architecture affecting the proton donor positioning for proton donation; and/or a dynamic mechanism wherein the intermediate compounds are brought into proper stereoelectronic alignment for the proton donation and cyclization geometry.

There now follows a description of the isolation, cloning, sequencing and functional characterization of citrus valencene synthase from *Citrus paradisi*. These examples are provided for the purpose of illustrating the invention, and are not to be considered as limiting.

Accordingly, one aspect of the present invention is an isolated nucleic acid comprising the nucleic acid sequence of SEQ ID NO 1. The nucleic acid is typically DNA, but can be RNA. If it is DNA, it is typically double-stranded, but can alternatively be single-stranded. Alternatively, it can be an RNA-DNA hybrid, i.e., either a complete or partial hybrid.

Another aspect of the present invention is an isolated nucleic acid that encodes the amino acid sequence of SEQ ID NO: 4. The nucleic acid is typically DNA, but can be RNA. If it is DNA, it is typically double-stranded, but can alternatively be single-stranded. Alternatively, it can be an RNA-DNA hybrid, i.e., either a complete or partial hybrid.

Another aspect of the present invention is an isolated nucleic acid encoding a protein that has the amino acid sequence of SEQ ID NO. 4 with 0 to 20 conservative amino acid substitutions, with the proviso that a conservative amino acid substitution is not made at amino acids 264, 273, 403, 404, 440, 444, 520, 527, and 528 in the protein that has the amino acid sequence of SEQ ID NO: 4, wherein the encoded protein specifically binds farnesyl pyrophosphate in a substantially hydrophobic pocket and has sesquiterpene synthase activity. Conservative amino acid substitutions are defined as above. Preferably, the nucleic acid sequence encodes a protein with 0 to 10 conservative amino acid substitutions. More preferably, the nucleic acid sequence encodes a protein with 0 to 5 conservative amino acid substitutions. Typically, the nucleic acid is DNA.

Yet another aspect of the present invention is an isolated nucleic acid encoding a protein that has the amino acid sequence of SEQ ID NO. 4 with 0 to 20 conservative amino acid substitutions, with the proviso that a conservative amino acid substitution is not made at amino acids 20, 264, 266, 270, 273, 298, 302, 372, 376, 401, 402, 403, 404, 407, 436, 440, 441, 444, 445, 448, 512, 515, 516, 519, 520, 527, 528, and 529 in the protein that has the amino acid sequence of SEQ ID NO: 4, wherein the encoded protein specifically binds farnesyl pyrophosphate in a substantially hydrophobic pocket and has sesquiterpene synthase activity. Preferably, the nucleic acid sequence encodes a protein with 0 to 10 conservative amino acid substitutions. More preferably, the nucleic acid sequence encodes a protein with 0 to 5 conservative amino acid substitutions. Typically, the nucleic acid is DNA.

Yet another aspect of the invention is an isolated nucleic acid that hybridizes to the nucleic acid of SEQ ID NO: 1 under stringent conditions with no more than about a 5% mismatch. Preferably, there is no more than about a 2% mismatch. More preferably, there is no more than about a 1% mismatch. Typically, the nucleic acid is DNA.

Yet another aspect of the invention is an isolated nucleic acid that encodes a protein that is at least 500 amino acids in length, that specifically binds farnesyl pyrophosphate in a hydrophobic pocket, and that has sesquiterpene synthase activity, wherein the nucleic acid includes SEQ ID NO. 5 and SEQ ID NO. 6. Typically, the nucleic acid is DNA.

Still another aspect of the invention is an isolated nucleic acid that encodes a protein that is at least 500 amino acids in length, that specifically binds farnesyl pyrophosphate in a hydrophobic pocket, and that has sesquiterpene synthase activity, wherein the nucleic acid includes SEQ ID NO. 5. Typically, the nucleic acid is DNA.

Still another aspect of the invention is an isolated nucleic acid that encodes a protein that includes amino acid residues 264 to 528 of SEQ ID NO. 4, wherein the protein specifically binds farnesyl pyrophosphate in a hydrophobic pocket and has sesquiterpene synthase activity. Typically, the nucleic acid is DNA.

As defined above, another embodiment of the invention is an isolated polypeptide having appropriate enzymatic activity, namely sesquiterpene synthase activity. These isolated polypeptides include, but are not necessary limited to:

(1) the polypeptide of SEQ ID NO: 4;
(2) a polypeptide that has the amino acid sequence of SEQ ID NO. 4 with 0 to 20 conservative amino acid substitutions, with the proviso that a conservative amino acid substitution is not made at amino acids 264, 273, 403, 404, 440, 444, 520, 527, and 528 in the protein that has the amino acid sequence of SEQ ID NO: 4, wherein the encoded protein specifically binds farnesyl pyrophosphate in a substantially hydrophobic pocket and has sesquiterpene synthase activity, preferably with 0 to 10 conservative amino acid substitutions, more preferably with 0 to 5 conservative amino acid substitutions;
(3) a polypeptide that has the amino acid sequence of SEQ ID NO. 4 with 0 to 20 conservative amino acid substitutions, with the proviso that a conservative amino acid substitution is not made at amino acids 20, 264, 266, 270, 273, 298, 302, 372, 376, 401, 402, 403, 404, 407, 436, 440, 441, 444, 445, 448, 512, 515, 516, 519, 520, 527, 528, and 529 in the protein that has the amino acid sequence of SEQ ID NO: 4, wherein the encoded protein specifically binds farnesyl pyrophosphate in a substantially hydrophobic pocket and has sesquiterpene synthase activity, preferably with 0 to 10 conservative amino acid substitutions, more preferably with 0 to 5 conservative amino acid substitutions;
(4) a polypeptide encoded by an isolated nucleic acid that hybridizes to the nucleic acid of SEQ ID NO: 1 under stringent conditions with no more than about a 5% mismatch, preferably no more than about a 2% mismatch, more preferably no more than about a 1% mismatch;
(5) a polypeptide that is at least 500 amino acids in length, that specifically binds farnesyl pyrophosphate in a hydrophobic pocket, and that has sesquiterpene synthase activity, wherein the sequence of the protein includes SEQ ID NO. 7 and SEQ ID NO. 8;
(6) a polypeptide that is at least 500 amino acids in length, that specifically binds farnesyl pyrophosphate in a hydrophobic pocket, and that has sesquiterpene synthase activity, wherein the sequence of the protein includes SEQ ID NO. 7; and (7) a polypeptide that includes amino acid residues 264 to 528 of SEQ ID NO. 4, wherein the protein specifically binds farnesyl pyrophosphate in a hydrophobic pocket and has sesquiterpene synthase activity.

Typically, the sesquiterpene synthase activity of proteins or polypeptides within the scope of the present invention is valencene synthase activity, but other sesquiterpenes can be synthesized by proteins or polypeptides within the scope of the present invention, either as the major reaction product or in side reactions.

Another embodiment of the present invention is a vector comprising a nucleic acid of the present invention, as described above, operably linked to at least one control sequence. Typically, the control sequence is a promoter or enhancer. As described above, such vectors are well known in the art.

Yet another embodiment of the present invention is a host cell transformed or transfected with a vector of the present invention. The host cell can be a prokaryotic cell or a eukaryotic cell, such as a bacterial cell, a yeast cell, a plant cell, or an animal cell, such as an insect cell or a mammalian cell. Typically, the host cell transformed or transfected with the vector is capable of expressing the protein or polypeptide encoded by the vector. Suitable host cells for expression of polypeptides of the invention include prokaryotes, yeast or higher eukaryotic cells. Appropriate cloning and expression vectors for use with bacterial, fungal, yeast, and mammalian cellular hosts are described, for example, in Pouwels et al., Cloning Vectors. A Laboratory Manual, Elsevier, N.Y., (1985). Cell-free translation systems could also be employed to produce the disclosed polypeptides using RNAs derived from DNA constructs disclosed herein.

Prokaryotes include gram negative or gram positive organisms, for example, E. coli or Bacilli. Suitable prokaryotic host cells for transformation include, for example, E. coli, Bacillus subtilis, Salmonella typhimurium, and various other species within the genera Pseudomonas, Streptomyces, and Staphylococcus. In a prokaryotic host cell, such as E. coli, the polypeptides can include a N-terminal methionine residue to facilitate expression of the 16 recombinant polypeptide in the prokaryotic host cell. The N-terminal methionine can be cleaved from the expressed recombinant polypeptide.

Examples of useful expression vectors for prokaryotic host cells include those derived from commercially available plasmids such as the cloning vector pET plasmids (Novagen, Madison, Wis., USA) or yet pBR322 (ATCC 37017). pBR322 contains genes for ampicillin and tetracycline resistance and thus provides simple means for identifying transformed cells. To construct an expression vector using pBR322, an appropriate promoter and a DNA sequence encoding one or more of the polypeptides of the invention are inserted into the pBR322 vector. Other commercially available vectors include, for example, pKK223-3 (Pharmacia Fine Chemicals, Uppsala, Sweden) and pGEM-1 (Promega Biotec, Madison, Wis., USA). Other commercially available vectors include those that are specifically designed for the expression of proteins; these would include pMAL-p2 and pMAL-c2 vectors that are used for the expression of proteins fused to maltose binding protein (New England Biolabs, Beverly, Mass., USA).

Promoter sequences commonly used for recombinant prokaryotic host cell expression vectors include bacteriophage T7 promoter (Studier F. W. and Moffatt B. A., J. Mol. Biol. 189:113, 1986), β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 19.80; and EP-A-36776), and tac promoter (Maniatis, MoLecular Cloning: A Laboratory Manual, Cold Spring Harbor Laboratory, p. 412. 1982). A particularly useful prokaryotic host cell expression system employs a phage λ PL promoter and a c1857ts thermolabile repressor sequence. Plasmid vectors available from the American Type Culture Collection ("ATCC"), which incorporate derivatives of the PL promoter, include plasmid pHUB2 (resident in E. coli strain JMB9 (ATCC 37092)) and pPLc28 (resident in E. coli RR1 (ATCC 53082)).

Polypeptides of the invention can also be expressed in yeast host cells, preferably from the Saccharomyces genus (e.g., S. cerevisiae). Other genera of yeast, such as Pichia or Kluyveromyces (e.g. K. lactis), can also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionine, 3-phosphoglycerate kinase (Hitzeman et al., J. Biol. Chem. 255:2073, 1980), or other glycolytic enzymes (Hess et al., J. Adv. Enzyme Reg. 7:149, 1968; and Holland et al., Biochem. 17:4900, 1978), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73, 657 or in Fleer et. al., Gene, 107:285-195 (1991); and van den Berg et. al., Bio/Technology, 8:135-139 (1990). Another alternative is the glucose-repressible ADH2 promoter described by Russell et al. (J. Biol. Chem. 258:2674, 1982) and Beier et al. (Nature 300:724, 1982). Shuttle vectors replicable in both yeast and E. coli can be constructed by inserting DNA sequences from pBR322 for selection and replication in E. coli (Ampr gene and origin of replication) into the above-described yeast vectors.

In one embodiment, mammalian or insect host cell culture systems are employed to express recombinant polypeptides of the invention. Baculovirus systems for production of heterologous proteins in insect cells are reviewed by Luckow and Summers, BioTechnology 6:47 (1988). Established cell lines of mammalian origin also can be employed. Examples of suitable mammalian host cell lines include the COS-7 line of monkey kidney cells (ATCC CRL 1651) (Gluzman et al., Cell 23:175, 1981), L cells, C1 27 cells, 3T3 cells (ATCC CCL 163), Chinese hamster ovary (CHO) cells, HeLa cells, and BHK (ATCC CRL 10) cell lines, and the CV-1/EBNA-1 cell line (ATCC CRL 10478) derived from the African green monkey kidney cell line CVI (ATCC CCL 70) as described by McMahan et al. (EMBO J. 10: 2821,1991).

In one embodiment, transfected DNA is integrated into a chromosome of a non-human organism such that a stable recombinant system results. Any chromosomal integration method known in the art may be used in the practice of the invention, including but not limited to, recombinase-mediated cassette exchange (RMCE), viral site specific chromosomal insertion, adenovirus, and pronuclear injection.

Yet another embodiment of the present invention is a non-human multicellular organism that is modified to harbor a nucleic acid of the present invention such that the nucleic acid can be expressed in the non-human multicellular organism. The non-human multicellular organism can be, but is not necessarily limited to, a plant or insect. The plant can be the tobacco plant. The non-human organism can be modified by any of the methods known in the art for gene transfer and the production of transgenic organisms, including, but not necessarily limited to, the use of delivery devices such as lipids and viral vectors, naked DNA, electroporation, and particle-mediated gene transfer.

Established methods for introducing DNA into mammalian cells have been described (Kaufinan, R. J., Large Scale Mammalian Cell Culture, 1990, pp. 15-69). Additional protocols using commercially available reagents, such as Lipofectamine (Gibco/BRL) or Lipofectamine-Plus, can be used to transfect cells (Felgner et al., Proc. Natl. Acad. Sci. USA 84:7413-7417, 1987). In addition, electroporation can be used to transfect mammalian cells using conventional procedures, such as those in Sambrook et al. Molecular Cloning: A Laboratory Manual, 2 ed. Vol. 1-3, Cold Spring Harbor Laboratory Press, 1989). Selection of stable transformants can be performed using resistance to cytotoxic drugs as a selection method. Kaufman et al., Meth. in Enzymology 185:487-511, 1990, describes several selection schemes, such as dihydrofolate reductase (DHFR) resistance. A suitable host strain for DHFR selection can be CHO strain DX-131 1, which is deficient in DHFR (Urlaub and Chasin, Proc. Natl. Acad. Sci. USA 77:4216-4220, 1980). A plasmid expressing the DHFR cDNA can be introduced into strain DX-131 1, and only cells that contain the plasmid can grow in the appropriate selective media.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and later promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273:113, 1978; Kaufinan, Meth. in Enzymology, 1990).

There are several methods known in the art for the creation of transgenic plants. These include, but are not limited to: electroporation of plant protoplasts, liposome-mediated transformation, polyethylene-glycol-mediated transformation, microinjection of plant cells, and transformation using viruses. In one embodiment, direct gene transfer by particle bombardment is utilized.

Direct gene transfer by particle bombardment provides an example for transforming plant tissue. In this technique a particle, or microprojectile, coated with DNA is shot through the physical barriers of the cell. Particle bombardment can be used to introduce DNA into any target tissue that is penetrable by DNA coated particles, but for stable transformation, it is imperative that regenerable cells be used. Typically, the particles are made of gold or tungsten. The particles are coated with DNA using either $CaCl_2$ or ethanol precipitation methods which are commonly known in the art.

DNA coated particles are shot out of a particle gun. A suitable particle gun can be purchased from Bio-Rad Laboratories (Hercules, Calif.). Particle penetration is controlled by varying parameters such as the intensity of the explosive burst, the size of the particles, or the distance particles must travel to reach the target tissue.

The DNA used for coating the particles may comprise an expression cassette suitable for driving the expression of the gene of interest that will comprise a promoter operably linked to the gene of interest.

Methods for performing direct gene transfer by particle bombardment are disclosed in U.S. Pat. No. 5,990,387 to Tomes et al., incorporated herein by this reference.

In one embodiment, the cDNAs of the invention may be expressed in such a way as to produce either sense or antisense RNA. Antisense RNA is RNA that has a sequence which is the reverse complement of the mRNA (sense RNA) encoded by a gene. A vector that will drive the expression of antisense RNA is one in which the ONA is placed in "reverse orientation" with respect to the promoter such that the non-coding strand (rather than the coding strand) is transcribed. The expression of antisense RNA can be used to down-modulate the expression of the protein encoded by the mRNA to which the antisense RNA is complementary. Vectors producing antisense RNAs could be used to make transgenic plants, as described above.

In one embodiment, transfected DNA is integrated into a chromosome of a non-human organism such that a stable recombinant systems results. Any chromosomal integration method known in the art may be used in the practice of the invention, including but not limited to, recombinase-mediated cassette exchange (RMCE), viral site specific chromosomal insertion, adenovirus, and pronuclear injection.

Still another embodiment of the invention is a method of producing a sesquiterpene synthase comprising the steps of:
(1) culturing a host cell transformed or transfected by a vector of the present invention under conditions in which the sesquiterpene synthase encoded by the vector is expressed; and
(2) isolating the sesquiterpene synthase expressed by the host cell.

Typically, the sesquiterpene synthase is valencene synthase, as described above.

Yet another embodiment of the invention is a method of producing a sesquiterpene comprising the steps of:
(1) reacting a protein or polypeptide of the present invention having sesquiterpene synthase enzymatic activity with farnesyl pyrophosphate under conditions in which the enzymatic activity catalyzes the formation of a sesquiterpene; and
(2) isolating the sesquiterpene formed in step (1).

Typically, the sesquiterpene synthase is a valencene synthase, in which case the sesquiterpene formed is valencene.

Still another embodiment of the present invention is a method of producing nootkatone. In one alternative of this embodiment, the method comprises the steps of:
(1) reacting a protein or polypeptide of the present invention having valencene synthase enzymatic activity with farnesyl pyrophosphate under conditions in which the enzymatic activity catalyzes the formation of valencene;
(2) reacting the valencene formed in step (1) by regiospecific hydroxylation and then oxidation to form nootkatone; and
(3) isolating the nootkatone produced.

The second step could be catalyzed by a single multifunctional hydroxylase or could be catalyzed by sequential enzyme mediated reactions.

Yet another embodiment of the invention is an antisense nucleic acid that is the complement of a nucleic acid according to the present invention as described above.

EXAMPLES

A cDNA of 1710 bp was prepared from fresh grapefruit via RT-PCR using non-degenerate primers designed to amplify from the translation start to stop sites of AF411120, then inserted into appropriate vectors for DNA sequencing and bacterial expression. For enzymological studies, the cDNA was inserted into a pET expression vector in-frame with an amino terminal hexa-histidine tag, and lysates of appropriately grown bacterial cultures used for nickel-affinity purification of the citrus cDNA encoded protein. The isolated citrus protein was approximately 30-40% pure as determined by Coomassie blue staining after SDS-PAGE and migrated as a 64 kD polypeptide (data not shown). The conceptual translation of the isolated cDNA predicted a protein of 548 amino acids having a molecular size of 63,646 daltons.

Example 1

Molecular Cloning of a Citrus Sesquiterpene Synthase cDNA

RNA was isolated from the juice vesicles of freshly harvested red grapefruit using TRIZOL reagent and following the manufacturer's protocol (Invitrogen Corp., Carlsbad, Calif.). Reverse transcription of the isolated RNA also followed manufacturer's protocol, and 10 µg of total RNA was reverse transcribed using Superscript II RNase H (Stratagene, La Jolla Calif.) and a reverse primer (18 nucleotides in length) complementary to the 3' end including the stop codon of the AF411120 sequence reported in Genbank. A full-length cDNA was then amplified using Pfu turbo Taq polymerase (Stratagene, La Jolla Calif.), more of the initial reverse primer, a forward primer (18 nucleotides in length) complementary to the 5' end initiating at the start codon, and an aliquot of the first strand cDNA using standard PCR conditions. An amplification fragment approximating the expected size of 1,800 bp was observed by agarose gel electrophoresis, T/A cloned into the pgem T-easy vector (Promega, Madison, Wis.) and then subjected to automated DNA sequencing using the BigDye terminator system with an ABI 310 sequencer. The sequence, which is shown in FIG. 5, was obtained from start to stop codons in duplicate and rectified with the reported sequence for the *Citrus x paradisi* putative terpene synthase mRNA. (Seq ID: 1). One nucleotide was found to be altered in the recovered cDNA, 1544 bp 5' to the ATG start site an A instead of a G was observed, converting codon 492 from specifying an aspartate to an arginine. Sequence analysis was performed using software tools available from the NCBI web site (www.ncbi.nlm.nih.gov) or using ClustalX.

Example 2

Expression of Citrus Valencene Synthase in *E. coli*

The Citrus valencene synthase (CVS) cDNA was inserted into an appropriate expression vector, pGEM to provide an amino-terminal hexa-histidyl tag for protein purification after expression of the putative valencene synthase cDNA in *E. coli*. The cDNA was re-amplified using PCR primers designed to amplify from the ATG start codon (5'-GGG-GAATTCATCTGGTCTGGAGAAACATTTCGTCC-3' (SEQ ID NO.: 2) to the TGA stop codon (5'-CCGCTCGAG-GAAGTATAGAACTAGTCGTCAAAATGG-3' (SEQ ID NO.:3)) and to provide restriction sites EcoRI and XhoI, (NEB, Beverly Mass.) respectively, using the pGEM-CVS plasmid as template under standard PCR conditions. The PCR product was digested with EcoRI and XhoI, purified using a QIAquick PCR purification kit (Qiagen, Valencia, Calif.), and ligated into a pET-28a(+) expression vector (Novagen, San Diego, Calif.) that had been digested with corresponding enzymes (NEB, Beverly Mass.), dephosphorylated with calf intestine alkaline phosphatase (Invitrogen, Carlsbad, Calif.), and purified with a QIAquick kit. Proper construction of the resulting expression vector was verified by DNA sequencing and subsequently referred to as the pET-28a(+)-CVS expression vector. The expression vector was transformed into BL21 (DE3) cells (Stratagene, La Jolla, Calif.), and grown in a 10 mL inoculate of LB Growth Media, using well known techniques. The cells were grown to an $OD_{600}$=1. IPTG (Sigma-Aldrich, St. Louis, Mo.) was used to induce expression of the putative valencene synthase gene. The transformed cells were incubated at 28° C. for four hours, centrifuged to form a pellet and the pellet was collected and resuspended in 1 mL of cyclase buffer (200 mM Tris-HCl, pH 7.5, 40 mM $MgCl_2$). Cells were then sonicated with three 10-sec bursts using a microtip ultrasonicator at 40% power and the lysate was centrifuged at 10,000×g for 10 minutes.

Figure 6:
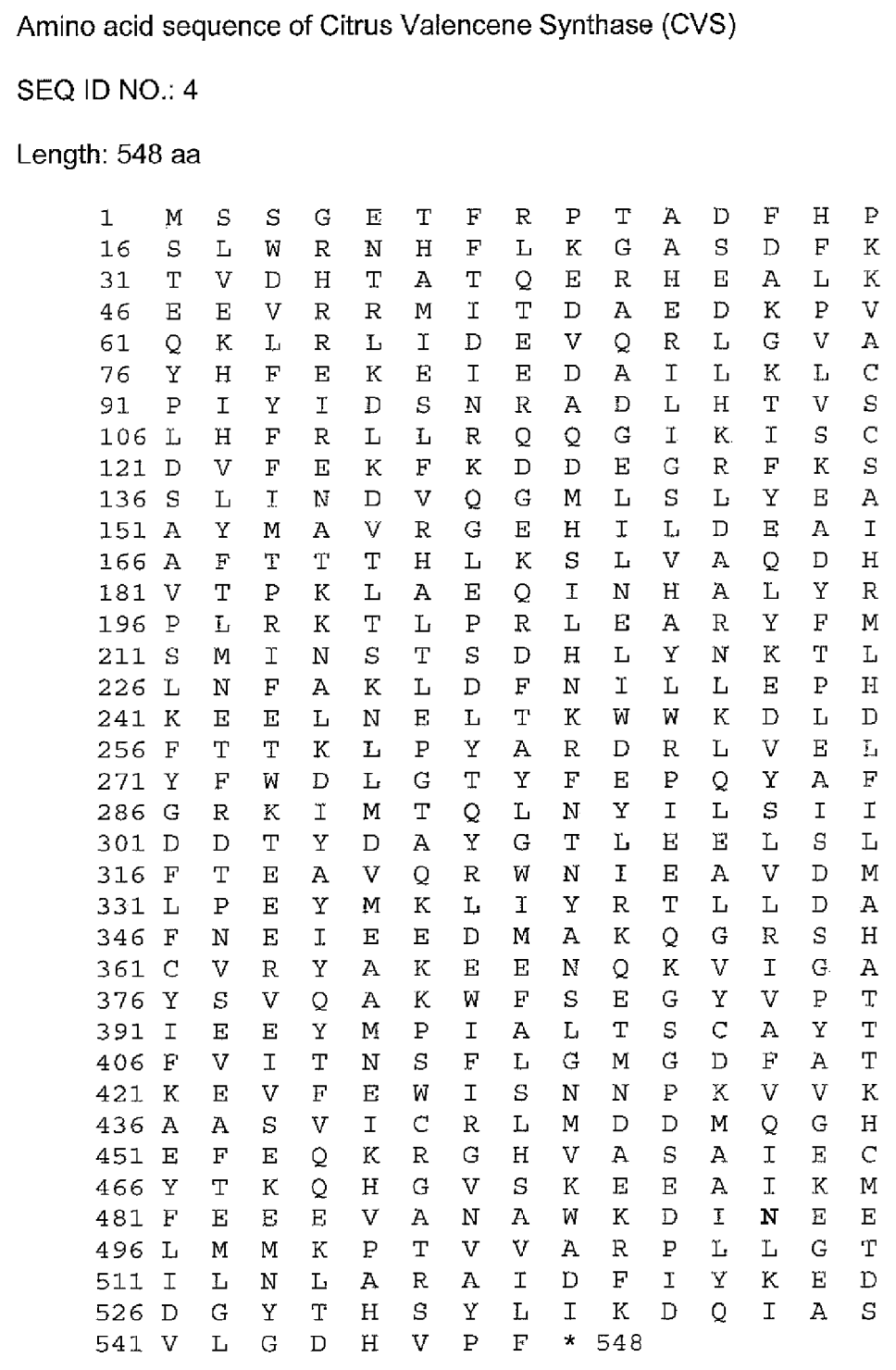

Samples of the lysate were divided and some samples were assayed for protein purity, while other samples were used in Example 3 below. For the protein purity assay, protein was purified by nickel affinity chromatography according to Mathis et al. (J. R. Mathis, K. Back, C. Starks, J. Noel, C. D. Poulter, J. Chappell, Biochem. 36 (1997) 8340-8348). Isolated CVS protein was approximately 30 to 40% pure based on the intensity of Coomassie blue staining of samples analyzed by SDS-PAGE. A protein sequencing reaction was performed via the Edman Degradation reaction performed using a Perkin Elmer Applied Biosystems Model 494 Procise protein/peptide sequencer with an on-line Perkin Elmer Applied Biosystems Model 140C PTH Amino Acid Analyzer. The protein sequence for the expressed CVS protein is shown in FIG. 6. (SEQ ID NO.; 4)

Figure 7:
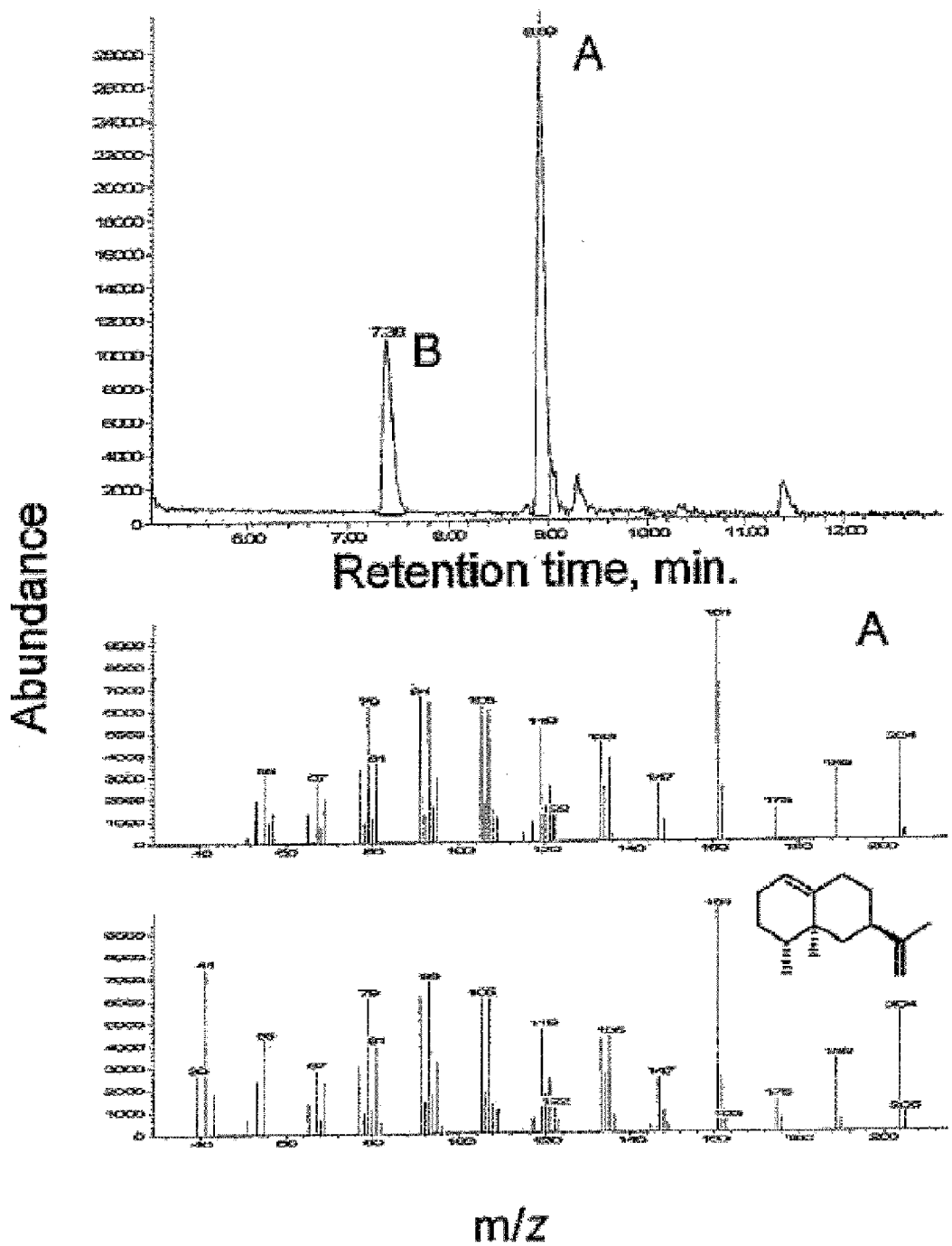
FIG. 7 illustrates reaction product analysis of citrus valencene synthase (CVS) incubated at pH 7.5. Lysate of *E. coli* expressing the CVS cDNA was incubated with FPP at pH 7.5 and total pentane extractable products evaluated by GC-MS (upper panel). The mass spectrum of the reaction product corresponding to peak A (middle panel) is compared to that of authentic valencene in the lower panel. The mass spectrum of peak B is identical to that for beta-elemene, the thermal-induced rearrangement product of germacrene A.

Partially purified protein was subsequently incubated with FPP at pH 7.5 using typical sesquiterpene synthase reaction conditions and the pentane extractable products examined by GC-MS (FIG. 7). Two compounds accounting for greater than 95% of the total reaction products dominated the GC profiles and were identified as beta-elemene (30%) and valencene (65%) on the basis of MS matches with authentic standards. The beta-elemene peak most certainly represents a thermal rearrangement product of germacrene A resulting from high temperature injection into the GC.

Example 3

Terpene Synthase Activity Assays and Reaction Product Identification

Small scale reactions of 50 µL were used for screening purposes and rate determinations. Reactions typically contained 200 mM Tris-HCl, pH 7.5, 40 mM $MgCl_2$, 0.5 µCi [1-3H]FPP, 25-30 µM FPP and 160 nM enzyme. For kinetic determinations, 10 µL aliquots of FPP (giving final concentrations of 0.7-23 µM) were rapidly mixed with 40 µL of enzyme solution at room temperature (23° C.) and allowed to incubate for 1 minute. The reactions were terminated by addition of 150 µL of a 100 mM KOH, 0.5 M EDTA stop solution. Reactions were extracted with 500 µL of hexane and an aliquot was taken for determination of radiolabeled hydrophobic product via liquid scintillation counting. Hexane extracted samples were not subject to silica chromatography prior to counting because background was minimal and synthase mutants could possibly produce reaction products containing alcohols, which would bind to silica. Kinetic constants were determined from direct fits of the Michaelis-Menton equation to the data using Graphpad Prism 2.01 software.

Figure 8:
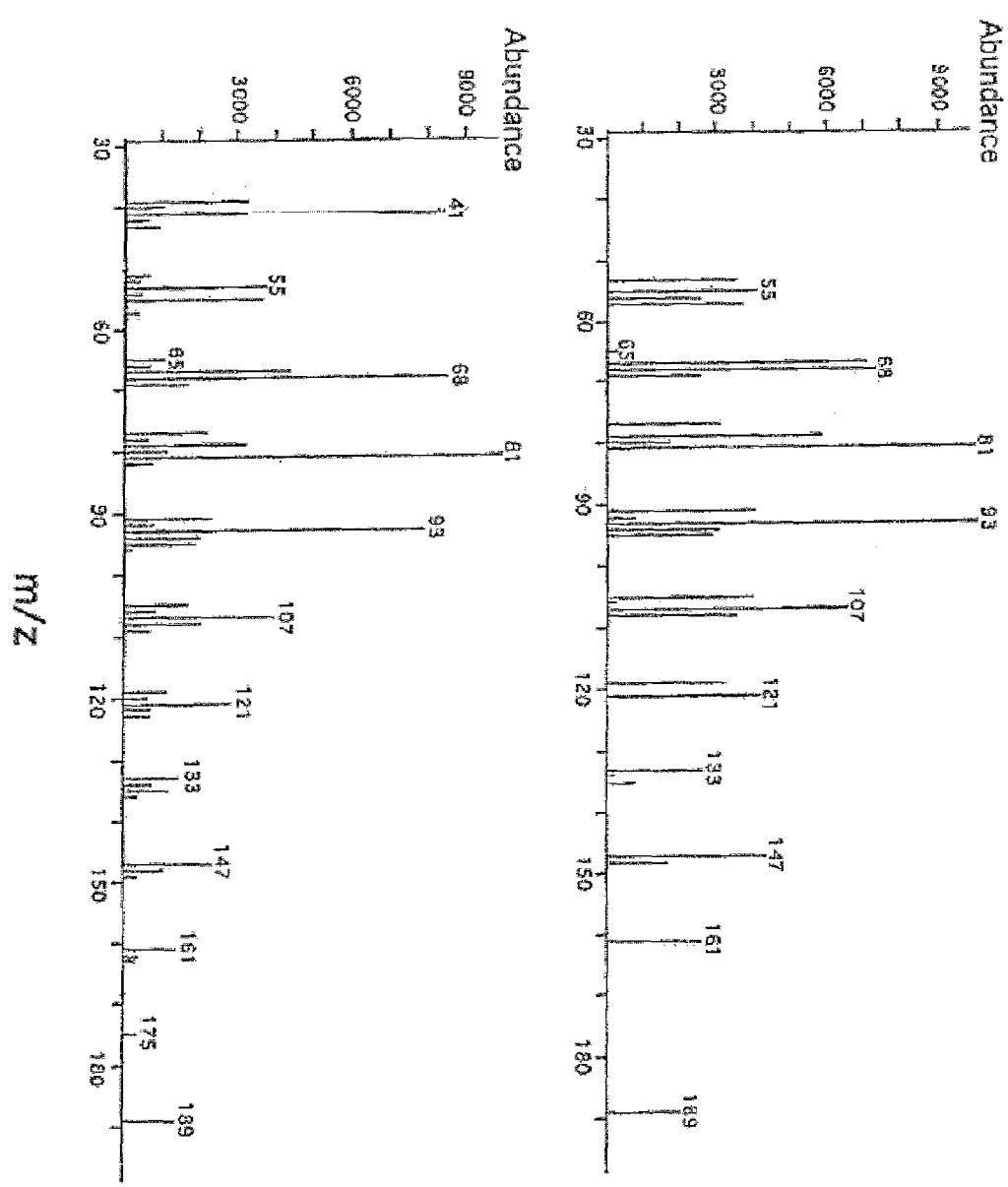
FIG. 8 illustrates a mass spectrum for the peak with a retention time of 7.38 minutes from FIG. 7 (top) compared to the spectra for beta-elemene published by the NIST library (bottom).
Figure 9:
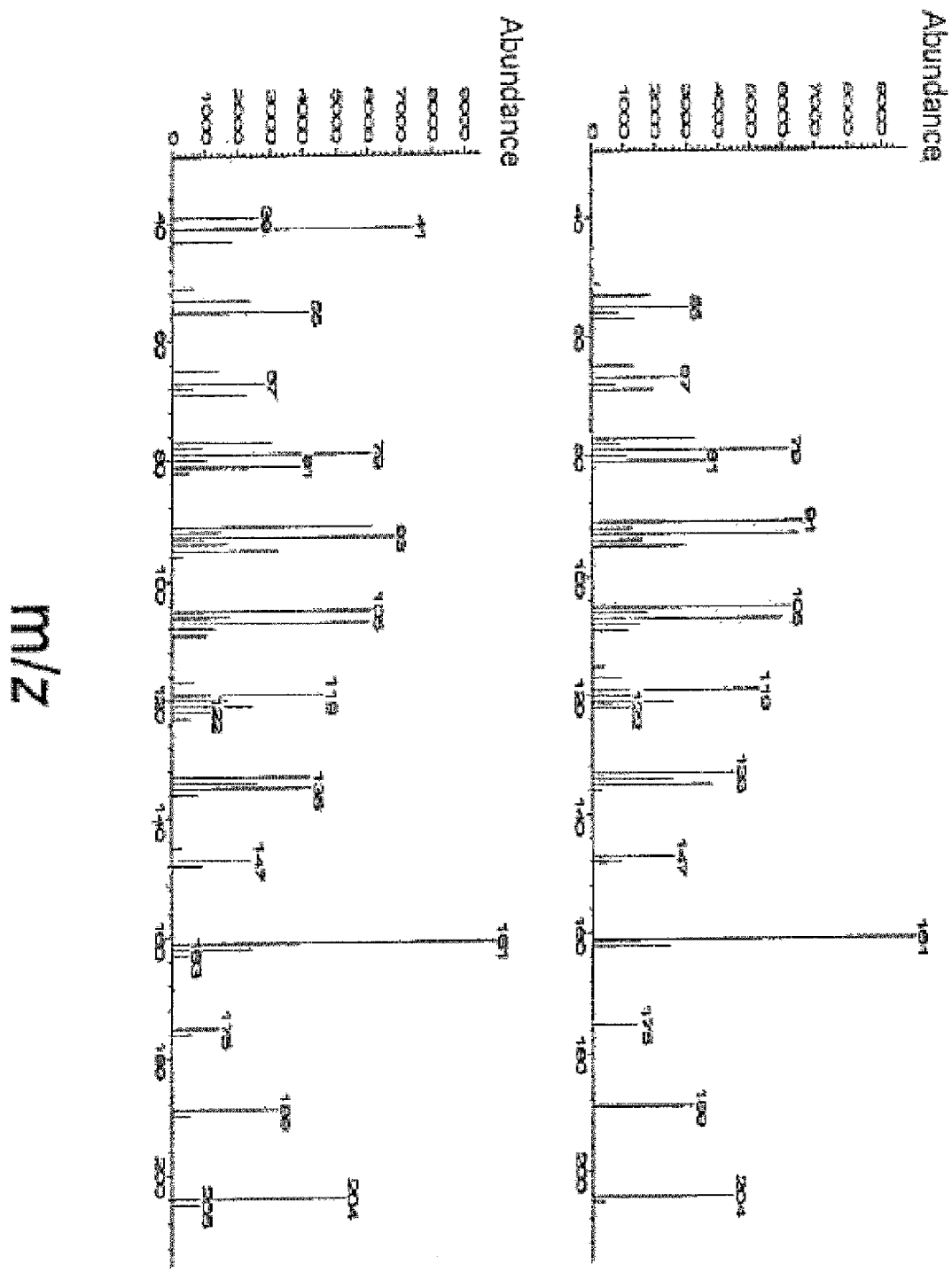
FIG. 9 illustrates mass spectrum for the peak with a retention time of 8.89 in FIG. 7 (top) compared to that for valencene purchased from Fluka Chemical Company (bottom).

Initial synthase reaction products were examined by GC-MS. Preparative reactions were performed similarly to the reactions described above except they were scaled to 2.5 mL and employed 2 µM of purified enzyme and 80 µM of unlabeled FPP. The reactions were incubated for 1 hr and then extracted twice with 2 mL of pentane. Pooled extracts were dried to 50 µL under a stream of nitrogen gas and 1 µL aliquots of this organic extract were analyzed by GC-MS using an HP-GCDplus (Hewlett-Packard, Palo Alto, Calif.) equipped with a DB-5 ms column, an injector temperature of 250° C. and the mass selective detector set to scan for ions within the range from 45 to 250 m/z. The GC was programmed to hold for 1 minute at 100° C., followed by a temperature ramp of 8° C./min to a final temperature of 270° C. The results are shown in FIG. 7. Spectra from this analysis was compared to the NIST library standard for beta-elemene (FIG. 8) and to that for a sample of valencene purchased from Fluka Chemical Company (FIG. 9).

The dominance of valencene as a reaction product under these conditions was sufficient to classify the *C. paradisi* cDNA as citrus valencene synthase, CVS. However, the amount of germacrene A, a putative reaction intermediate (FIG. 1), generated by the CVS enzyme was atypical relative to previous studies with TEAS and HPS. Neither of these enzymes release appreciable amounts of reaction intermediates. Further consideration of the acidic conditions likely to exist within juice vesicles/sacs where sesquiterpenes accumulate in citrus fruit suggested that the CVS enzyme might have a pH optimal different from other terpene synthases.

Figure 10:
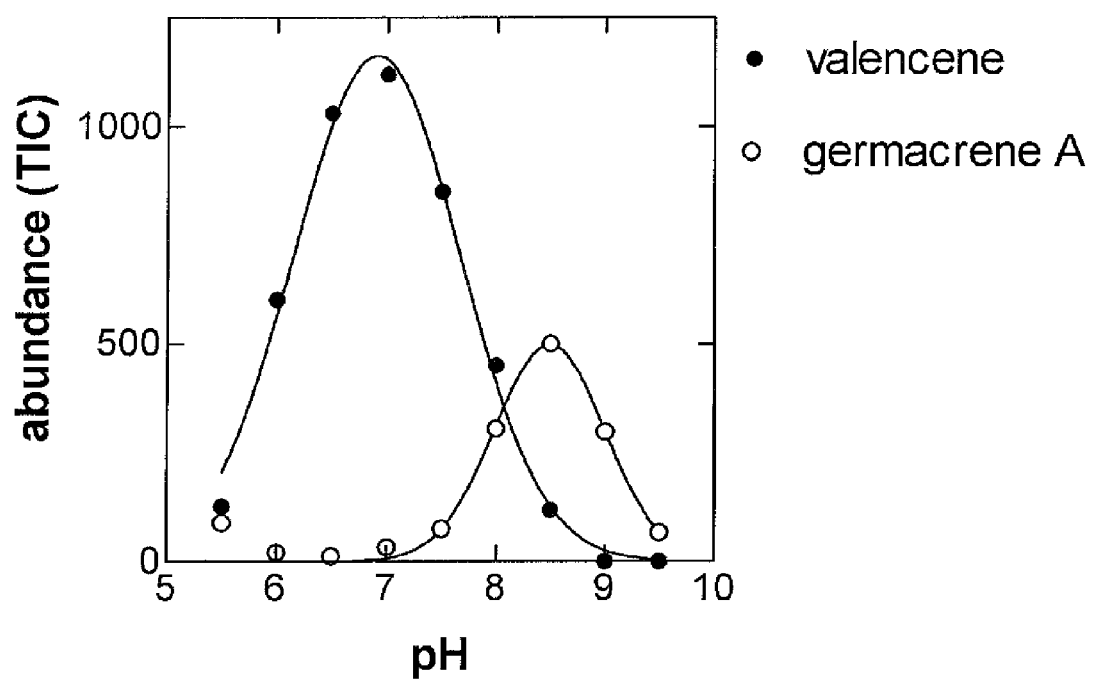
FIG. 10 illustrates that the reaction product specificity of citrus valencene synthase (CVS) is pH dependent. Partially purified synthase isolated from *E. coli* expressing the CVS cDNA was incubated with FPP at the indicated pH values and ethylacetate extracts were examined directly by GC-MS. Absolute values for valencene (solid symbols) and germacrene A (measured as the thermally rearranged product β-elemene) (open symbols) are reported and represent greater than 95% of the total reaction products at all pHs.

As shown in FIG. 10, virtually no germacrene A was detected as a reaction product between pH 6.0 to 7.0, with optimal valencene biosynthesis occurring at pH 7.0 (FIG. 10). In contrast, germacrene A biosynthesis was optimal at pH 8.5 with a relatively sharp transition point from valence as the dominate reaction product to germacrene A at pH 8.0.

Example 4 pH Dependence Assays

Reactions to determine pH dependence were performed in glass GC-vials with 100 nM of purified enzyme, 20 mM MgCl2, 50 µM FPP (Echelon; Salt Lake City, Utah), and 100 mM buffer at various pH values; total reaction volume 500 µL. The buffers were chosen within one pH unit of the buffer's pKa (pH 5-5.5, acetate; pH 6-7, MES; pH 7.5-9, Tris; pH 9.5-10, ethanolamine; pH 10.5, CAPS). Reactions were allowed to proceed at room temperature for 30 min prior to overlaying with 500 µL of ethylacetate, vortexing for 10 sec, then direct analysis of the reaction products using an HP 6890 gas chromatograph with a 5973 mass spectrometer (Agilent Technologies, Palo Alto, Calif.) with an auto-sampler programmed to remove 1 µL samples only from the organic phase. GC separations were performed on a 5%-phenyl-methylpolysiloxane column (J&W Scientific, Folsom, Calif.) of 30 m×0.25 mm i.d.×0.25 m thickness with He as the carrier gas at 2 mL/min and a temperature gradient of 10° C./min from 50° C. (5-min hold) to 180° C. (4-min hold). GC/MS data was analyzed using HP-Chemstation software (version B.01.00) and integration of terpene peaks used for quantification.

As seen in FIG. 10, a pH dependent transition between valencene and germacrene A biosynthesis occurs at approximately pH 8.2. Inventors interpreted this as a titration point for the protonation of germacrene A. This pH value is close to the pKa value of 8.3-8.5 for free cysteine, which is involved in the second protonation step of the chemical cascade catalyzed by TEAS. Those results demonstrated that when C440 of TEAS was mutated to alanine, a robust germacrene A synthetic activity resulted. In combination with the sequence data provided in SEQ ID NO.: 7 and SEQ ID NO.: 8, it is apparent that germacrene synthases consistently differ from CVS, TEAS and HPS by the absence of cysteine at position 440 in their putative active site while Y520, previously implicated in the same protonation step, is conserved. The observation of germacrene A as a reaction product and the pH dependence for its synthesis are consistent with its intermediacy in the reaction catalyzed by CVS.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

We claim:

1. An isolated nucleic acid comprising the nucleic acid sequence of SEQ ID NO: 1.

2. The isolated nucleic acid of claim 1 wherein the nucleic acid is DNA.

3. An isolated nucleic acid that encodes the amino acid sequence of SEQ ID NO: 4.

4. The isolated nucleic acid of claim 3 wherein the nucleic acid is DNA.

* * * * *

SEQUENCE LISTING

<160> NUMBER OF SEQ ID NOS: 8

<210> SEQ ID NO 1
<211> LENGTH: 1647
<212> TYPE: DNA
<213> ORGANISM: Citrus X paradisi

<400> SEQUENCE: 1

```
atgtcgtctg gagaaacatt tcgtcctact gcagatttcc atcctagttt atggagaaac    60
catttcctca aggtgcttc tgatttcaag acagttgatc atactgcaac tcaagaacga   120
cacgaggcac tgaaagaaga ggtaaggaga atgataacag atgctgaaga taagcctgtt   180
cagaagttac gcttgattga tgaagtacaa cgcctggggg tggcttatca ctttgagaaa   240
gaaatagaag atgcaatact aaaattatgt ccaatctata ttgacagtaa tagagctgat   300
ctccacaccg tttcccttca ttttcgattg cttaggcagc aaggaatcaa gatttcatgt   360
gatgtgtttg agaagttcaa agatgatgag ggtagattca agtcatcgtt gataaacgat   420
gttcaaggga tgttaagttt gtacgaggca gcatacatgg cagttcgcgg agaacatata   480
ttagatgaag ccattgcttt cactaccact cacctgaagt cattggtagc tcaggatcat   540
gtaaccccta agcttgcgga acagataaat catgctttat accgtcctct tcgtaaaacc   600
ctaccaagat tagaggcgag gtattttatg tccatgatca attcaacaag tgatcattta   660
tacaataaaa ctctgctgaa ttttgcaaag ttagatttta acatattgct agagccgcac   720
aaggaggaac tcaatgaatt aacaaagtgg tggaaagatt tagacttcac tacaaaacta   780
ccttatgcaa gagacagatt agtggagtta tattttggg atttagggac atacttcgag   840
cctcaatatg catttgggag aaagataatg acccaattaa attacatatt atccatcata   900
gatgatactt atgatgcgta tggtacactt gaagaactca gcctctttac tgaagcagtt   960
caaagatgga atattgaggc cgtagatatg cttccagaat acatgaaatt gatttacagg  1020
acactcttag atgcttttaa tgaaattgag gaagatatgg ccaagcaagg aagatcacac  1080
tgcgtacgtt atgcaaaaga ggagaatcaa aaagtaattg gagcatactc tgttcaagcc  1140
aaatggttca gtgaaggtta cgttccaaca attgaggagt atatgcctat tgcactaaca  1200
agttgtgctt acacattcgt cataacaaat tccttccttg gcatgggtga ttttgcaact  1260
aaagaggttt ttgaatggat ctccaataac cctaaggttg taaaagcagc atcagttatc  1320
tgcagactca tggatgacat gcaaggtcat gagtttgagc agaagagagg acatgttgcg  1380
tcagctattg aatgttacac gaagcagcat ggtgtctcta aggaagaggc aattaaaatg  1440
tttgaagaag aagttgcaaa tgcatggaaa gatattaacg aggagttgat gatgaagcca  1500
accgtcgttg cccgaccact gctcgggacg attcttaatc ttgctcgtgc aattgatttt  1560
atttacaaag aggacgacgg ctatacgcat tcttacctaa ttaaagatca aattgcttct  1620
gtgctaggag accacgttcc attttga                                       1647
```

<210> SEQ ID NO 2
<211> LENGTH: 35
<212> TYPE: DNA
<213> ORGANISM: Citrus X paradisi

<400> SEQUENCE: 2

```
ggggaattca tctggtctgg agaaacattt cgtcc                               35
```

<210> SEQ ID NO 3
<211> LENGTH: 36
<212> TYPE: DNA
<213> ORGANISM: Citrus X paradisi

<400> SEQUENCE: 3
ccgctcgagg aagtatagaa ctagtcgtca aaatgg          36

<210> SEQ ID NO 4
<211> LENGTH: 548
<212> TYPE: PRT
<213> ORGANISM: Citrus X paradisi

<400> SEQUENCE: 4

```
Met Ser Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Glu Asp Ala Ile Leu Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Tyr Asn Lys Thr
    210                 215                 220

Leu Leu Asn Phe Ala Lys Leu Asp Phe Asn Ile Leu Leu Glu Pro His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Asp Asp Thr Tyr
    290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335
```

Leu Ile Tyr Arg Thr Leu Leu Asp Ala Phe Asn Glu Ile Glu Glu Asp
    340                 345                 350

Met Ala Lys Gln Gly Arg Ser His Cys Val Arg Tyr Ala Lys Glu Glu
            355                 360                 365

Asn Gln Lys Val Ile Gly Ala Tyr Ser Val Gln Ala Lys Trp Phe Ser
        370                 375                 380

Glu Gly Tyr Val Pro Thr Ile Glu Glu Tyr Met Pro Ile Ala Leu Thr
385                 390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
            420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
    450                 455                 460

Cys Tyr Thr Lys Gln His Gly Val Ser Lys Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
            500                 505                 510

Asn Leu Ala Arg Ala Ile Asp Phe Ile Tyr Lys Glu Asp Asp Gly Tyr
        515                 520                 525

Thr His Ser Tyr Leu Ile Lys Asp Gln Ile Ala Ser Val Leu Gly Asp
    530                 535                 540

His Val Pro Phe
545

<210> SEQ ID NO 5
<211> LENGTH: 1647
<212> TYPE: DNA
<213> ORGANISM: Citrus X paradisi
<220> FEATURE:
<221> NAME/KEY: misc_feature
<222> LOCATION: (1)..(789)
<223> OTHER INFORMATION: n is a, c, g, or t
<220> FEATURE:
<221> NAME/KEY: misc_feature
<222> LOCATION: (793)..(816)
<223> OTHER INFORMATION: n is a, c, g, or t
<220> FEATURE:
<221> NAME/KEY: misc_feature
<222> LOCATION: (820)..(1206)
<223> OTHER INFORMATION: n is a, c, g, or t
<220> FEATURE:
<221> NAME/KEY: misc_feature
<222> LOCATION: (1213)..(1320)
<223> OTHER INFORMATION: n is a, c, g, or t
<220> FEATURE:
<221> NAME/KEY: misc_feature
<222> LOCATION: (1324)..(1332)
<223> OTHER INFORMATION: n is a, c, g, or t
<220> FEATURE:
<221> NAME/KEY: misc_feature
<222> LOCATION: (1336)..(1563)
<223> OTHER INFORMATION: n is a, c, g, or t
<220> FEATURE:
<221> NAME/KEY: misc_feature
<222> LOCATION: (1567)..(1575)
<223> OTHER INFORMATION: n is a, c, g, or t
<220> FEATURE:
<221> NAME/KEY: misc_feature
<222> LOCATION: (1579)..(1581)

```
<223> OTHER INFORMATION: n is a, c, g, or t
<220> FEATURE:
<221> NAME/KEY: misc_feature
<222> LOCATION: (1588)..(1647)
<223> OTHER INFORMATION: n is a, c, g, or t

<400> SEQUENCE: 5
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnna gannnnnnnn nnnnnnnnnn nnnnnntggn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnngctt acnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
tgcnnnnnnn nngatnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnntacnnnn nnnnngacnn ntatacgnnn nnnnnnnnnn nnnnnnnnnn nnnnnnnnnn    1620
nnnnnnnnnn nnnnnnnnnn nnnnnnn                                         1647

<210> SEQ ID NO 6
<211> LENGTH: 1647
<212> TYPE: DNA
<213> ORGANISM: Citrus X paradisi
<220> FEATURE:
<221> NAME/KEY: misc_feature
<222> LOCATION: (1)..(36)
<223> OTHER INFORMATION: n is a, c, g, or t
<220> FEATURE:
<221> NAME/KEY: misc_feature
<222> LOCATION: (40)..(795)
<223> OTHER INFORMATION: n is a, c, g, or t
<220> FEATURE:
<221> NAME/KEY: misc_feature
```

```
<222> LOCATION: (799)..(807)
<223> OTHER INFORMATION: n is a, c, g, or t
<220> FEATURE:
<221> NAME/KEY: misc_feature
<222> LOCATION: (811)..(891)
<223> OTHER INFORMATION: n is a, c, g, or t
<220> FEATURE:
<221> NAME/KEY: misc_feature
<222> LOCATION: (895)..(903)
<223> OTHER INFORMATION: n is a, c, g, or t
<220> FEATURE:
<221> NAME/KEY: misc_feature
<222> LOCATION: (907)..(1113)
<223> OTHER INFORMATION: n is a, c, g, or t
<220> FEATURE:
<221> NAME/KEY: misc_feature
<222> LOCATION: (1117)..(1125)
<223> OTHER INFORMATION: n is a, c, g, or t
<220> FEATURE:
<221> NAME/KEY: misc_feature
<222> LOCATION: (1129)..(1200)
<223> OTHER INFORMATION: n is a, c, g, or t
<220> FEATURE:
<221> NAME/KEY: misc_feature
<222> LOCATION: (1207)..(1218)
<223> OTHER INFORMATION: n is a, c, g, or t
<220> FEATURE:
<221> NAME/KEY: misc_feature
<222> LOCATION: (1222)..(1308)
<223> OTHER INFORMATION: n is a, c, g, or t
<220> FEATURE:
<221> NAME/KEY: misc_feature
<222> LOCATION: (1312)..(1323)
<223> OTHER INFORMATION: n is a, c, g, or t
<220> FEATURE:
<221> NAME/KEY: misc_feature
<222> LOCATION: (1327)..(1335)
<223> OTHER INFORMATION: n is a, c, g, or t
<220> FEATURE:
<221> NAME/KEY: misc_feature
<222> LOCATION: (1339)..(1344)
<223> OTHER INFORMATION: n is a, c, g, or t
<220> FEATURE:
<221> NAME/KEY: misc_feature
<222> LOCATION: (1348)..(1539)
<223> OTHER INFORMATION: n is a, c, g, or t
<220> FEATURE:
<221> NAME/KEY: misc_feature
<222> LOCATION: (1543)..(1548)
<223> OTHER INFORMATION: n is a, c, g, or t
<220> FEATURE:
<221> NAME/KEY: misc_feature
<222> LOCATION: (1555)..(1560)
<223> OTHER INFORMATION: n is a, c, g, or t
<220> FEATURE:
<221> NAME/KEY: misc_feature
<222> LOCATION: (1564)..(1587)
<223> OTHER INFORMATION: n is a, c, g, or t
<220> FEATURE:
<221> NAME/KEY: misc_feature
<222> LOCATION: (1591)..(1647)
<223> OTHER INFORMATION: n is a, c, g, or t

<400> SEQUENCE: 6
nnnnnnnnnn nnnnnnnnnn nnnnnnnnnn nnnnnttcn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
```

```
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnagann nnnnnnntta nnnnnnnnnn nnnnnnnnnn nnnnnnnnnn    840
nnnnnnnnnn nnnnnnnnnn nnnnnnnnnn nnnnnnnnnn nnnnnnnnnn ntccnnnnnn    900
nnngatnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnngtannnn nnnnntacnn nnnnnnnnnn   1140
nnnnnnnnnn nnnnnnnnnn nnnnnnnnnn nnnnnnnnnn nnnnnnnnnn nnnnnnnnnn   1200
agttgtnnnn nnnnnnnngt cnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnngc annnnnnnnn   1320
nnnagannnn nnnnngacnn nnnnggtnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnc ttnnnnnngc aattnnnnnn   1560
attnnnnnnn nnnnnnnnnn nnnnnnncat nnnnnnnnnn nnnnnnnnnn nnnnnnnnnn   1620
nnnnnnnnnn nnnnnnnnnn nnnnnn                                        1647

<210> SEQ ID NO 7
<211> LENGTH: 548
<212> TYPE: PRT
<213> ORGANISM: Citrus X paradisi
<220> FEATURE:
<221> NAME/KEY: misc_feature
<222> LOCATION: (1)..(263)
<223> OTHER INFORMATION: Xaa can be any naturally occurring amino acid
<220> FEATURE:
<221> NAME/KEY: misc_feature
<222> LOCATION: (265)..(272)
<223> OTHER INFORMATION: Xaa can be any naturally occurring amino acid
<220> FEATURE:
<221> NAME/KEY: misc_feature
<222> LOCATION: (274)..(402)
<223> OTHER INFORMATION: Xaa can be any naturally occurring amino acid
<220> FEATURE:
<221> NAME/KEY: misc_feature
<222> LOCATION: (405)..(440)
<223> OTHER INFORMATION: Xaa can be any naturally occurring amino acid
<220> FEATURE:
<221> NAME/KEY: misc_feature
<222> LOCATION: (442)..(444)
<223> OTHER INFORMATION: Xaa can be any naturally occurring amino acid
<220> FEATURE:
<221> NAME/KEY: misc_feature
<222> LOCATION: (446)..(521)
<223> OTHER INFORMATION: Xaa can be any naturally occurring amino acid
<220> FEATURE:
<221> NAME/KEY: misc_feature
<222> LOCATION: (523)..(525)
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
```

<220> FEATURE:
<221> NAME/KEY: misc_feature
<222> LOCATION: (530)..(548)
<223> OTHER INFORMATION: Xaa can be any naturally occurring amino acid

<400> SEQUENCE: 7

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Arg Xaa Xaa Xaa Xaa Xaa Xaa Xaa
            260                 265                 270

Trp Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380
```

```
Xaa Xaa Xaa Xaa Xaa Xaa Xaa Xaa Xaa Xaa Xaa Xaa Xaa Xaa Xaa
385                 390                 395                 400

Xaa Xaa Ala Tyr Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Cys Xaa Xaa Xaa Asp Xaa Xaa Xaa
    435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Tyr Xaa Xaa Xaa Asp Xaa Tyr
    515                 520                 525

Thr Xaa Xaa Xaa Xaa Xaa Xaa Xaa Xaa Xaa Xaa Xaa Xaa Xaa Xaa
    530                 535                 540

Xaa Xaa Xaa Xaa
545

<210> SEQ ID NO 8
<211> LENGTH: 548
<212> TYPE: PRT
<213> ORGANISM: Citrus X paradisi
<220> FEATURE:
<221> NAME/KEY: misc_feature
<222> LOCATION: (1)..(12)
<223> OTHER INFORMATION: Xaa can be any naturally occurring amino acid
<220> FEATURE:
<221> NAME/KEY: misc_feature
<222> LOCATION: (14)..(265)
<223> OTHER INFORMATION: Xaa can be any naturally occurring amino acid
<220> FEATURE:
<221> NAME/KEY: misc_feature
<222> LOCATION: (267)..(269)
<223> OTHER INFORMATION: Xaa can be any naturally occurring amino acid
<220> FEATURE:
<221> NAME/KEY: misc_feature
<222> LOCATION: (271)..(297)
<223> OTHER INFORMATION: Xaa can be any naturally occurring amino acid
<220> FEATURE:
<221> NAME/KEY: misc_feature
<222> LOCATION: (299)..(301)
<223> OTHER INFORMATION: Xaa can be any naturally occurring amino acid
<220> FEATURE:
<221> NAME/KEY: misc_feature
<222> LOCATION: (303)..(371)
<223> OTHER INFORMATION: Xaa can be any naturally occurring amino acid
<220> FEATURE:
<221> NAME/KEY: misc_feature
<222> LOCATION: (373)..(375)
<223> OTHER INFORMATION: Xaa can be any naturally occurring amino acid
<220> FEATURE:
<221> NAME/KEY: misc_feature
<222> LOCATION: (377)..(400)
<223> OTHER INFORMATION: Xaa can be any naturally occurring amino acid
<220> FEATURE:
<221> NAME/KEY: misc_feature
<222> LOCATION: (403)..(406)
<223> OTHER INFORMATION: Xaa can be any naturally occurring amino acid
<220> FEATURE:
<221> NAME/KEY: misc_feature
<222> LOCATION: (408)..(436)
<223> OTHER INFORMATION: Xaa can be any naturally occurring amino acid
<220> FEATURE:
```

<220> FEATURE:
<221> NAME/KEY: misc_feature
<222> LOCATION: (438)..(441)
<223> OTHER INFORMATION: Xaa can be any naturally occurring amino acid
<220> FEATURE:
<221> NAME/KEY: misc_feature
<222> LOCATION: (443)..(445)
<223> OTHER INFORMATION: Xaa can be any naturally occurring amino acid
<220> FEATURE:
<221> NAME/KEY: misc_feature
<222> LOCATION: (447)..(448)
<223> OTHER INFORMATION: Xaa can be any naturally occurring amino acid
<220> FEATURE:
<221> NAME/KEY: misc_feature
<222> LOCATION: (450)..(513)
<223> OTHER INFORMATION: Xaa can be any naturally occurring amino acid
<220> FEATURE:
<221> NAME/KEY: misc_feature
<222> LOCATION: (515)..(516)
<223> OTHER INFORMATION: Xaa can be any naturally occurring amino acid
<220> FEATURE:
<221> NAME/KEY: misc_feature
<222> LOCATION: (519)..(520)
<223> OTHER INFORMATION: Xaa can be any naturally occurring amino acid
<220> FEATURE:
<221> NAME/KEY: misc_feature
<222> LOCATION: (522)..(529)
<223> OTHER INFORMATION: Xaa can be any naturally occurring amino acid
<220> FEATURE:
<221> NAME/KEY: misc_feature
<222> LOCATION: (531)..(548)
<223> OTHER INFORMATION: Xaa can be any naturally occurring amino acid

<400> SEQUENCE: 8

```
Xaa Xaa Xaa Xaa Xaa Xaa Xaa Xaa Xaa Xaa Xaa Xaa Phe Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240
```

```
Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Arg Xaa Xaa Xaa Leu Xaa Xaa
            260                 265             270

Xaa Xaa Xaa Xaa Xaa Xaa Xaa Xaa Xaa Xaa Xaa Xaa Xaa Xaa Xaa
            275             280                 285

Xaa Xaa Xaa Xaa Xaa Xaa Xaa Xaa Ser Xaa Xaa Xaa Asp Xaa Xaa
            290                 295             300

Xaa Xaa Xaa Xaa Xaa Xaa Xaa Xaa Xaa Xaa Xaa Xaa Xaa Xaa Xaa
305             310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
            340             345                 350

Xaa Xaa Xaa Xaa Xaa Xaa Xaa Xaa Xaa Xaa Xaa Xaa Xaa Xaa Xaa
            355                 360                 365

Xaa Xaa Xaa Val Xaa Xaa Xaa Tyr Xaa Xaa Xaa Xaa Xaa Xaa Xaa
            370             375                 380

Xaa Xaa Xaa Xaa Xaa Xaa Xaa Xaa Xaa Xaa Xaa Xaa Xaa Xaa Xaa
385             390                 395                 400

Ser Cys Xaa Xaa Xaa Xaa Val Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Ala Xaa Xaa Xaa Xaa Arg Xaa Xaa Xaa Asp Xaa Xaa
            435                 440             445

Gly Xaa Xaa Xaa Xaa Xaa Xaa Xaa Xaa Xaa Xaa Xaa Xaa Xaa
            450                 455             460

Xaa Xaa Xaa Xaa Xaa Xaa Xaa Xaa Xaa Xaa Xaa Xaa Xaa Xaa Xaa
465             470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Leu Xaa Xaa Ala Ile Xaa Xaa Ile Xaa Xaa Xaa Xaa Xaa Xaa Xaa
            515                 520                 525

Xaa His Xaa Xaa Xaa Xaa Xaa Xaa Xaa Xaa Xaa Xaa Xaa Xaa Xaa
            530                 535             540

Xaa Xaa Xaa Xaa
545
```